(12) United States Patent
Das

(10) Patent No.: US 9,493,838 B2
(45) Date of Patent: Nov. 15, 2016

(54) BIOMARKERS AND TREATMENTS FOR HEART FAILURE

(71) Applicant: Beth Israel Deaconess Medical Center, Inc., Boston, MA (US)

(72) Inventor: Saumya Das, Lexington, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 14/434,537

(22) PCT Filed: Oct. 10, 2013

(86) PCT No.: PCT/US2013/064308
§ 371 (c)(1),
(2) Date: Apr. 9, 2015

(87) PCT Pub. No.: WO2014/059126
PCT Pub. Date: Apr. 17, 2014

(65) Prior Publication Data
US 2015/0329907 A1    Nov. 19, 2015

Related U.S. Application Data

(60) Provisional application No. 61/712,044, filed on Oct. 10, 2012.

(51) Int. Cl.
*C12Q 1/68*    (2006.01)
*C12N 15/113*    (2010.01)

(52) U.S. Cl.
CPC ........... *C12Q 1/6883* (2013.01); *C12N 15/113* (2013.01); *C12N 2310/141* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2005/0261218 A1 | 11/2005 | Esau et al. |
| 2009/0143326 A1 | 6/2009 | Obad et al. |
| 2009/0306181 A1 | 12/2009 | Ikeda et al. |
| 2009/0326051 A1 | 12/2009 | Corey et al. |

FOREIGN PATENT DOCUMENTS

WO    WO-2008/061537 A2    5/2008

OTHER PUBLICATIONS

International Search Report for International Application No. PCT/US2013/064308, mailed Jan. 29, 2014 (4 pages).
International Preliminary Report on Patentability for International Application No. PCT/US2013/064308, dated Apr. 14, 2015 (9 pages).

*Primary Examiner* — Kimberly Chong
(74) *Attorney, Agent, or Firm* — Clark & Elbing LLP; Kristina Bieker-Brady

(57) ABSTRACT

The invention features methods to predict the response to a cardiac therapy in a patient suffering from a cardiac disease, e.g., heart failure. The invention features measurement expression of biomarkers that help in this prediction. The invention also features methods for treatment of cardiac diseases. These methods include cardiac resynchronization therapy and miRNA based therapeutics.

8 Claims, 26 Drawing Sheets

A

B

A

B

A

B

A

B

A

B

Figure 17- con't.
B
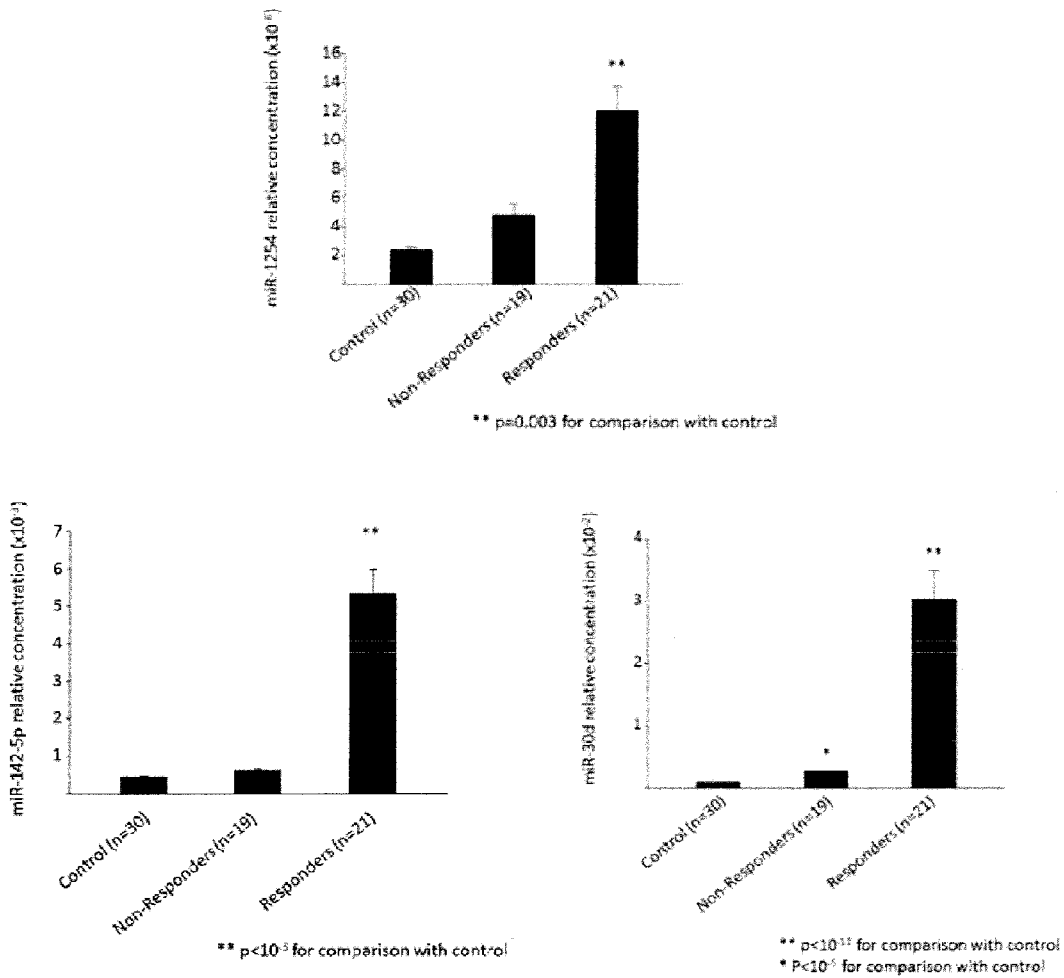

A

B

BIOMARKERS AND TREATMENTS FOR HEART FAILURE

CROSS-REFERENCE TO RELATED APPLICATIONS

This application claims the benefit of the filing date of U.S. Provisional Application No. 61/712,044, which was filed on Oct. 10, 2012, the contents of which are hereby incorporated by reference in its entirety.

FIELD OF THE INVENTION

The invention features methods and kits for predicting response to a cardiac therapy in a patient suffering from a cardiac disease. The invention also features methods for treatment of cardiac diseases.

BACKGROUND OF THE INVENTION

Systolic heart failure (HF) is an increasing contributor to disease burden and healthcare expenditure in the United States. Approximately 5 million Americans have heart failure and 550,000 new cases are reported annually. 42% of cases end in mortality within 5 years of admission for heart failure. Congestive heart failure (CHF) is a significant public health problem with more than 20 million people affected worldwide. The prevalence of CHF is on the rise with increasing incidences of coronary artery disease, particularly amongst an aging population in the United States.

Patients with HF who have delayed depolarization of the lateral wall of their left ventricle (LV) have impaired contractile function due to dyssynchronous electrical and mechanical activation. Dyssynchronous heart failure (DHF) is associated with abnormal wall stress and alteration of gene expression differentially between the late-activated lateral wall and early-activated anterior wall. One contributor to left ventricular dysfunction and CHF is ventricular dyssychrony. Dyssynchronous ventricular contractions occur as a result of damage to the heart's conduction system due to cardiomyopathy, ischemic damage, or pacing. The myocardium in the late-contracting areas is subjected to increased wall stress, decreased coronary perfusion, and up-regulation of genes involved in cardiac hypertrophy, fibrosis, and apoptosis. Ventricular dyssynchrony has been shown to lead to a decline in cardiac function and approximately 35-50% of medication-refractory heart failure patients have evidence of dyssynchrony.

Treatments for HF include administration of beta-blockers, which decreases mortality by 30-35%; or administration of ACE inhibitors, which decreases mortality by 16-30%. While large clinical trials have shown that medications and device-based therapies lead to improved outcomes in patients with HF, a significant proportion of patients do not adequately respond to these therapies, e.g., 50-60% of patients, have medication refractory HF. Generally, patients with impaired contractile function due to dyssynchronous left ventricular (LV) electrical and mechanical activation (termed dyssynchronous heart failure, DHF) benefit from cardiac resynchronization therapy (CRT) by simultaneously pacing their septal and lateral LV. CRT has been shown to decrease CHF hospitalizations, improve quality of life and CHF symptoms, and decrease mortality. Current guidelines indicate that CRT should be used in patients with symptomatic CHF (New York Heart Association (NYHA) Class II-IV), a low ejection fraction (EF) less than 35%, and a QRS duration>130 ms. Unfortunately, even in appropriately selected patients, approximately 30% of patients do not derive benefit from CRT, and algorithms to predict response to CRT using currently available clinical and biochemical variables have not been satisfactory. Therefore, novel approaches for predicting response to CRT are urgently needed, and would help identify patients who would benefit from this procedure.

Although retrospective studies have identified some clinical variables such as diabetes, female gender, and QRS duration on the ECG, as predictors of response to CRT, none of these variables can adequately explain differences between responders and non-responders. Thus there is a need in the field for methods that can predict whether a patient will be a 'responder' or a 'non-responder' to a cardiac therapy, e.g., cardiac resynchronization therapy, in order to better determine a treatment course for the patient.

SUMMARY OF THE INVENTION

The invention features a method for predicting response to a cardiac therapy in a patient suffering from a cardiac disease (e.g., heart failure or dyssynchronous heart failure), wherein the method includes the steps of: i) collecting a sample from a patient; ii) determining if the level of expression of a biomarker having at least 85% (e.g., 90%, 95%, 98%, or 100%) sequence identity to the sequence of SEQ ID NO: 1, 27, or 33, is changed relative to a control sample; and iii) predicting a response to the cardiac therapy in the patient, based on the level of expression of the biomarker.

The invention also features a method a for predicting response to a cardiac therapy in a patient suffering from a cardiac disease, wherein the method includes the steps of: i) determining if the level of expression of a biomarker, having at least 85% sequence identity to the sequence of SEQ ID NO: 1, 27, 33, in a sample collected from a patient, is changed relative to a control sample; and ii) predicting a response to the cardiac therapy in the patient, based on the level of expression of the biomarker.

In one aspect of any of the above methods of the invention, an increase in the level of expression of the biomarker (e.g., an increase of 20%, 30%, 50%, 80%, 100%, 200%, 300%, 500%, 800%, 1000% of the biomarker) may be predictive of a positive response to a cardiac therapy, e.g. CRT. Alternatively, a decrease in the level of expression (e.g., a decrease of 20%, 30%, 50%, 80%, 100%, 200%, 300%, 500%, 800%, 1000% of the biomarker) may indicate a poor response to a cardiac therapy, e.g., CRT. A positive response can be, for example, an improvement in LV ejection fraction by >10% at a 6 month follow-up, post-therapy. A positive response can also be alleviation of the symptoms of the cardiac disease and/or a delay in mortality. In another aspect of the methods of the invention, the method can further comprise administering a cardiac therapy to the patient based on a prediction of a positive response to the cardiac therapy.

In one aspect of the invention, the prediction of a positive or poor response to a cardiac therapy is done prior to a first cardiac therapy. Alternatively, the prediction can be done after the first cardiac therapy. In yet another aspect of the method of the invention, the prediction can be done any time during the course of cardiac therapy (e.g., 2 weeks, 1 month, 2 months, 6 months, or 1 year).

In another aspect of any of the above methods of the invention, the methods further comprises suggesting a cardiac therapy to said patient based on a prediction of a positive response to said cardiac therapy, where the cardiac therapy is cardiac resynchronization therapy (CRT) or a miRNA based therapy.

The invention features a method for treatment of a cardiac disease in a patient, wherein the method includes the steps of: i) collecting a sample from a patient; ii) determining if the level of expression of a biomarker having at least 85% sequence identity to the sequence of SEQ ID NO: 1, 27, or 33 is changed relative to a control sample; iii) predicting a response to the cardiac therapy in the patient based on the level of expression of the biomarker; and iv) administering a cardiac therapy (e.g., CRT or a miRNA based therapy) to the patient based on a prediction of a positive response to the cardiac therapy.

The invention also features a method for treatment of a cardiac disease in a patient, where the method includes the steps of: i) determining if the level of expression of a biomarker having at least 85% sequence identity to the sequence of SEQ ID NO: 1, 27, or 33 in a sample collected from a patient, is changed relative to a control sample; ii) predicting a response to the cardiac therapy in the patient based on the level of expression of the biomarker; and iii) administering a cardiac therapy (e.g., CRT or a miRNA based therapy) to the patient based on a prediction of a positive response to the cardiac therapy.

In one aspect of the above methods of treatment, a level of expression of the biomarker that is increased (e.g., an increase by 20%, 30%, 50%, 80%, 100%, 200%, 300%, 500%, 800%, 1000%, relative to control sample) is predictive of a positive response to the cardiac therapy. In another aspect, a cardiac therapy (e.g., CRT or a miRNA based therapy) is administered to the patient upon a prediction of a positive response to the cardiac therapy based on increased expression of the biomarker.

In one aspect of the methods of the invention, the biomarker can be miRNA-30d, miRNA-1254, or miRNA-766. The sample from a patient can be a blood sample or a plasma sample. The sample can include nucleic acid molecules, and the level of expression of the biomarker can be determined using a quantitative reverse transcription-polymerase chain reaction (qRT-PCR) to amplify the nucleic acid molecules.

The invention also features a kit that includes reagents for collecting nucleic acid molecules from a sample from a patient; reagents for amplifying the nucleic acid molecules collected from the sample to produce an amplified sample; and reagents for measuring the level of expression (e.g., using qRT-PCR) of a biomarker having at least 85% sequence identity to the sequence of SEQ ID NO: 1, 27, or 33. In one aspect of the kit of the invention, the biomarker of the kit can have the sequence of miRNA-30d (SEQ ID NO: 1) or the precursor-miR-30d (SEQ ID NO: 2). In another aspect of the invention, the biomarker of the kit can have the sequence of miRNA-1254 (SEQ ID NO:27) or the precursor-miR-1254 (SEQ ID NO:30). In yet another aspect of the invention, the biomarker of the kit can have the sequence of miRNA-766 (SEQ ID NO:33) or the precursor-miR-766 (SEQ ID NO:34). In another aspect of the kit of the invention, the kit may further include instructions for predicting response to a cardiac therapy based on level of expression of the biomarker in the sample from the patient.

In any of the methods of the invention, the cardiac therapy can be the administration of CRT. Alternatively, or additionally, the therapy can be a miRNA based therapy (e.g., the administration of a therapeutic that targets a miRNA having at least 85% sequence identity to the sequence of SEQ ID NO: 1, 27, or 33, or a compound that comprises a nucleic acid having at least 85% sequence identity to the sequence of SEQ ID NO: 1 (e.g., miRNA-30d), SEQ ID NO:27 (e.g., miRNA-1254), or SEQ ID NO:33 (e.g., miRNA-766). Alternatively, the therapeutic can include a compound that comprises a nucleic acid precursor for miRNA-30d, miRNA-1254, or miRNA-766. In some embodiments, the therapeutic can include a compound that causes a change (e.g., an increase) in the level of expression of miRNA-30d, miRNA-1254, or miRNA-766 in a patient. The miRNA based therapy can include administering a nucleic acid having the sequence of SEQ ID NO: 1, SEQ ID NO: 2, SEQ ID NO:27, SEQ ID NO:30, SEQ ID NO:33, or SEQ ID NO:34.

In yet another aspect of the methods of treatment, the method can further include the steps of: i) collecting a sample from a patient; and ii) determining the level of expression of a biomarker, having at least 85% sequence identity to the sequence of SEQ ID NO: 1, 27, or 33 to monitor the efficacy of the miRNA based therapeutic.

In any of the methods, kits or compositions of the invention, the biomarker or miRNA based therapy has 90%, 95%, 98%, 99%, or 100% identity with the sequence of SEQ ID NOs: 1, 2, 27, 30, 33, or 34.

In any of the above methods of the inventions, there are particular embodiments. In one embodiment, the biomarker has at least 85% sequence identity to the sequence of SEQ ID NO: 1. In a second embodiment, the biomarker has at least 85% sequence identity to the sequence of SEQ ID NO: 27. In a third embodiment, the biomarker has at least 85% sequence identity to the sequence of SEQ ID NO:33. In a fourth embodiment, the biomarker has at least 85% sequence identity to the sequence of SEQ ID NO:1 and 27. In a fifth embodiment, the biomarker has at least 85% sequence identity to the sequence of SEQ ID NO:1 and 33. In a sixth embodiment, the biomarker has at least 85% sequence identity to the sequence of SEQ ID NO:27 and 33. In a last embodiment, the biomarker has at least 85% sequence identity to the sequence of SEQ ID NO:1, 27, and 33.

DEFINITIONS

"Biomarker" as used herein indicates a gene or other portion of a subject's genetic material that is expressed in a form that can be measured (e.g., a miRNA or a precursor-miRNA, a protein, and a mRNA) and whose expression indicates a prediction of a positive or poor response to a cardiac therapy in a patient.

"Cardiac therapy" as used herein indicates a therapy that is administered to a patient to reduce symptoms or delay mortality due to a cardiac disease.

"Control sample" as used herein indicates a sample from a normal patient, or a patient who has undergone a cardiac therapy, resulting in any combination of alleviation of symptoms of the cardiac disease, reduction in risk of mortality, or delay in mortality.

"Level of expression" as used herein indicates the amount of a biomarker present in a sample relative to the amount of that biomarker in a control sample. By "increase" in "level of expression" means an increased amount of a biomarker present in a sample relative to the amount of that biomarker in a control sample. By "decrease" in "level of expression" means a decreased amount of a biomarker present in a sample relative to the amount of that biomarker in a control sample.

"miRNA" as used herein indicates a small non-coding RNA that is incorporated into RNA induced silencing complexes and plays an important role in post-transcriptional gene regulation either by transcriptional degradation or translational repression of mRNA.

"Plasma" as used herein indicates the straw-colored/pale-yellow liquid component of blood that normally contains blood cells in whole blood in suspension. Blood plasma is prepared by spinning a tube of fresh blood containing an anti-coagulant in a centrifuge until the blood cells fall to the bottom of the tube. The blood plasma is then poured or drawn off.

"Response" as used herein indicates a patient's response to a cardiac therapy, e.g., a response can be a positive response resulting in an improvement in LV ejection fraction by >10% at a 6 month follow-up, post-therapy, e.g., post-CRT.

"Sequence identity" as used herein indicates a nucleic acid sequence that has the same nucleic acid sequence as a reference sequence, or has a specified percentage of nucleotides that are the same at the corresponding location within a reference sequence when the two sequences are optimally aligned. For example a nucleic acid sequence may have at least 50%, 60%, 70%, 75%, 80%, 85%, 90%, 95%, 96%, 97%, 98%, 99%, or 100% identity to the reference nucleic acid sequence. The length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

"Treatment" as used herein indicates administering to a subject or living organism a therapy, e.g. cardiac resynchronization therapy, a compound (e.g., a drug), or some other form of medical intervention to treat a cardiac disease or symptoms of the heart.

"Therapeutic" or "miRNA based therapy" as used herein indicates a compound that targets a miRNA having at least 85% sequence identity to the sequence of SEQ ID NO: 1. The therapeutic can include a compound that comprises a nucleic acid having at least 85% (e.g., 90%, 95%, 98%, or 100%) sequence identity to the sequence of SEQ ID NO: 1 (e.g., miRNA-30d). The therapeutic can also include a compound that comprises a nucleic acid precursor for miRNA-30d (e.g., having the sequence of SEQ ID NO: 2). Alternatively, the therapeutic can include a compound that causes a change (e.g., an increase) in the level of expression of miRNA-30d in a patient. The miRNA based therapy can also include administering a nucleic acid having the sequence of SEQ ID NO: 1, SEQ ID NO: 2, or SEQ ID NOs: 27-32.

"miR-30d" as used herein indicates a mature miR-30d (e.g., a nucleic acid having a sequence at least 85% (e.g., 90%, 95%, 98%, 100%) identity to the sequence of SEQ ID NO: 1 (UGUAAACAUCCCCGACUGGAAG)) or a miR-30d precursor (e.g., a nucleic acid having a sequence at least 85% (e.g., 90%, 95%, 98%, 100%) identity to the sequence of SEQ ID NO: 2 (GUUGUUGUAAACAUCCCCGACUG-GAAGCUGUAAGACACAGCUAAGCUUUCAGUCA-GAUGUUUGC UGCUAC)).

"miR-1254" as used herein indicates a mature miR-1254 (e.g., a nucleic acid having a sequence at least 85% (e.g., 90%, 95%, 98%, 100%) identity to the sequence of SEQ ID NO: 27 (AGCCUGGAAGCUGGAGCCUGCAGU)) or a miR-1254 precursor (e.g., a nucleic acid having a sequence at least 85% (e.g., 90%, 95%, 98%, 100%) identity to the sequence of SEQ ID NO:30 (GGUGGGAGGAUUGC-UUGAGCCUGGAAGCUGGAGCCUGCAGUGAAC-UAUCAUUGUGCCACUGUA CUCCAGCCUAG-GCAACAAAAUGAAAUCCUGUCUA)).

"miR-142-5p" as used herein indicates a mature miR-142-5p (e.g., a nucleic acid having a sequence at least 85% (e.g., 90%, 95%, 98%, 100%) identity to the sequence of SEQ ID NO: 28 (CAUAAAGUAGAAAGCACUACU)) or a miR-142-5p precursor (e.g., a nucleic acid having a sequence at least 85% (e.g., 90%, 95%, 98%, 100%) identity to the sequence of SEQ ID NO:31 (GACAGUGCAGU-CACCCAUAAAGUAGAAAGCACU-ACUAACAGCACUGGAGGGUGUAGUGUUUCCU ACUUUAUGGAUGAGUGUACUGUG)).

"miR-29c" as used herein indicates a mature miR-29c (e.g., a nucleic acid having a sequence at least 85% (e.g., 90%, 95%, 98%, 100%) identity to the sequence of SEQ ID NO: 29 (UGACCGAUUUCUCCUGGUGUUC)) or a miR-29c precursor (e.g., a nucleic acid having a sequence at least 85% (e.g., 90%, 95%, 98%, 100%) identity to the sequence of SEQ ID NO:32 (AUCUCUUACACAGGCUGAC-CGAUUUCUCCUGGU-GUUCAGAGUCUGUUUUUGUCUAGCACCAUUU GAAAUCGGUUAUGAUGUAGGGGGA)).

"miR-766" as used herein indicates a mature miR-766 (e.g., a nucleic acid having a sequence at least 85% (e.g., 90%, 95%, 98%, 100%) identity to the sequence of SEQ ID NO: 33 (ACUCCAGCCCCACAGCCUCAGC)) or a miR-766 precursor (e.g., a nucleic acid having a sequence at least 85% (e.g., 90%, 95%, 98%, 100%) identity to the sequence of SEQ ID NO:34 (GCAUCCUCAGGACCUGGGC-UUGGGUGGUAGGAGGAAUUGGUGCUGGUCUUU-CAUUUUGGAUUU GACUCCAGCCCCACAGCCUCA-GCCACCCCAGCCAAUUGUCAUAGGAGC)).

"miRNA" and "miR" are used interchangeably herein and is meant to refer to the microRNAs described herein.

DETAILED DESCRIPTION OF THE INVENTION

Figure 1:
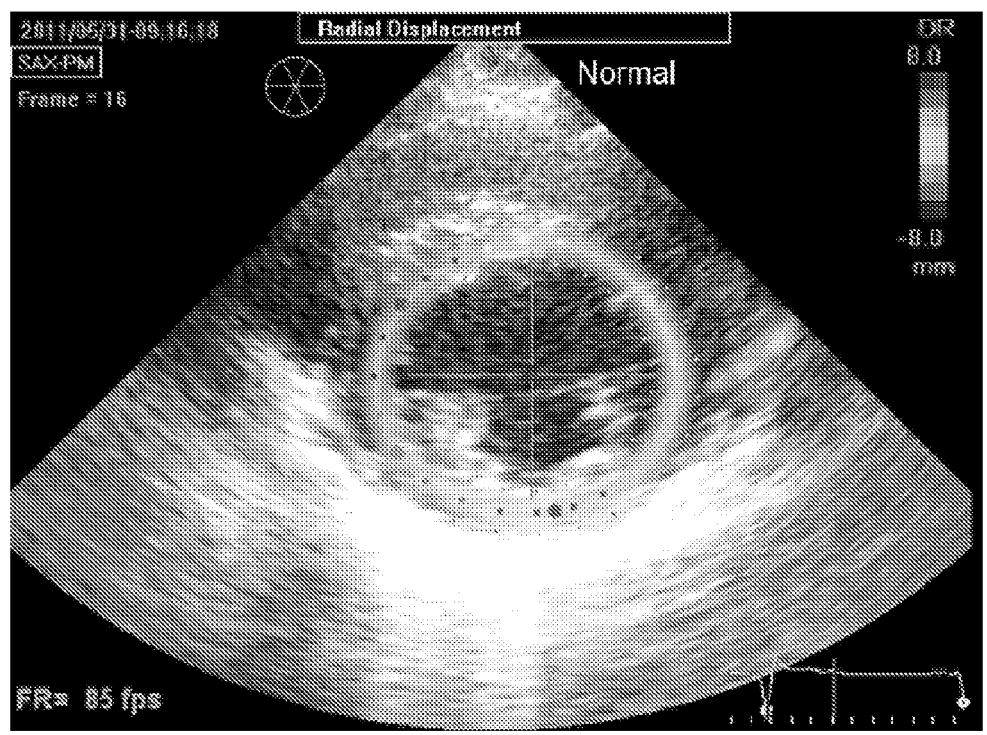
FIG. 1 is an image of an echocardiogram with superimposed strain patterns showing synchronized strain in a normal heart.
Figure 1:
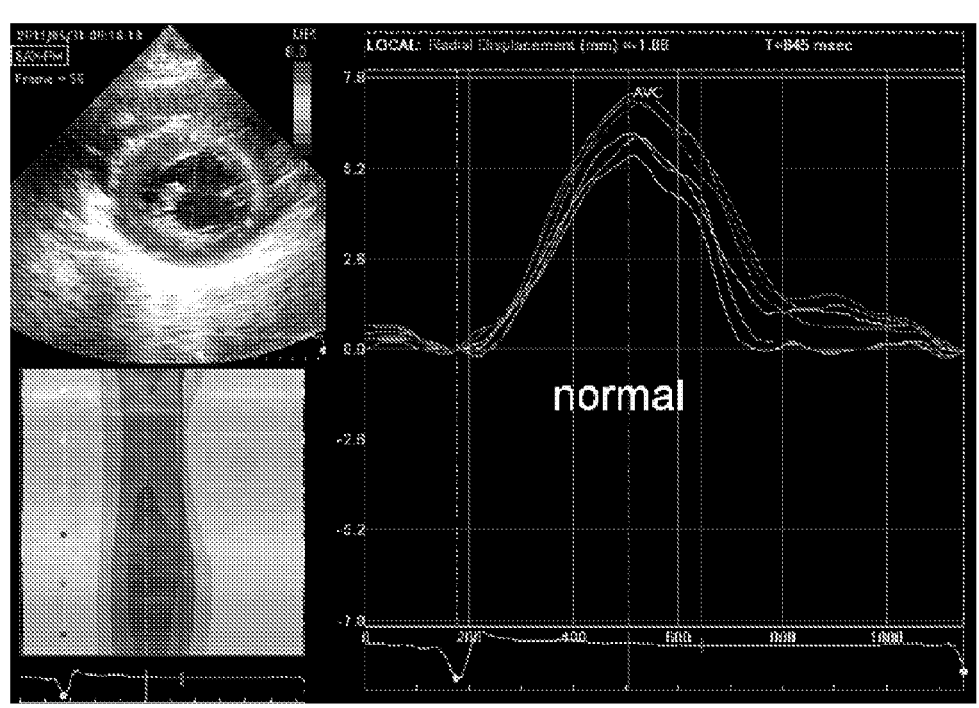

In general, the invention is based on the discovery that plasma levels of a novel microRNA, miR-30d, is significantly increased at baseline in patients classified as 'responders' to cardiac resynchronization therapy (CRT) compared to 'non-responders.' In patients with dyssynchronous heart failure (DHF) undergoing CRT, miR-30d prospectively predicts response to CRT independent of known clinical variables, and is enriched in the coronary sinus compared to peripheral blood, suggesting a cardiac origin.

The invention features methods for determining the expression level of a biomarker from a patient sample and predicting the response of a patient suffering from a cardiac disease (e.g., heart failure (HF)) to a cardiac therapy (e.g., CRT or miRNAs therapy). The invention also features a kit which includes reagents and instructions for predicting a response to a cardiac therapy in a patient suffering from a cardiac disease, e.g., heart failure. The invention also features methods for the treatment of a cardiac disease, e.g., heart failure, by a cardiac therapy, e.g., CRT or miRNA based therapy.

Accordingly, plasma miRNAs, such as miR-30d, may serve as prognostic biomarkers to predict left ventricular (LV) remodeling in response to CRT. Using a miRNA array for 766 miRNAs, it was discovered that five plasma miRNAs were significantly different at baseline (prior to implant) between echocardiographic responders and non-responders to CRT at six months. In an independent prospective cohort of 40 patients followed after CRT implantation, three miRNA candidates were validated as predictors of echocardiographic response to CRT at six months, and one of these, miR-30d, was an independent determinant of CRT response in a multivariable regression model incorporating clinical variables and miRNA levels. It was shown that miRN-30d is up regulated in the lateral wall of dyssynchronous ventricles in a canine model, appears to be regulated by cardiomyocyte (CM) stretch, and promotes physiological growth in CMs in vitro. The mitogen-associated protein kinase-4 kinase (MAP4K4), a down-stream mediator or tumor necrosis factor (TNF) signaling, was found to be a target of miR-30d and, miR-30d affords protection against TNF-α induced up-regulation of MAP4K4 and subsequent apoptosis in primary cultured CMs. Thus, miR-30d is a circulating cardiac-secreted miRNA that predicts LV remodeling following CRT response and may be cardioprotective against apoptosis.

miRNAs in the Cardiovascular System

MicroRNAs (miRNAs) are small (22-24 bp) RNA molecules that function as potent suppressors of gene expression. A single miRNA can down-regulate the expression of multiple genes and affect multiple gene expression and signaling pathways. miRNAs have been linked to cardiac hypertrophy, fibrosis, neoplasm, and insulin resistance. Recently, miRNAs were discovered in circulating plasma, likely as a consequence of secretion by multiple tissues. Plasma miRNAs appear to be stable over long periods of time, and thus are attractive candidates for biomarkers.

Indeed miRNAs have now been identified as diagnostic biomarkers for cardiovascular diseases including coronary artery disease and congestive heart failure. More intriguingly, several recent studies have suggested that apart from simply being disease reporters, some plasma miRNAs may play a functional role in atherosclerosis or ventricular remodeling after myocardial infarction.

In the cardiovascular system, exosomes and microvesicles (termed 'EMV') can be released from endothelial cells and cardiomyocytes, and the associated miRNAs/miRNAs can alter gene expression in other cell types. Therefore, EMVs and their contents including miRNAs may represent a novel mechanism in disease pathogenesis. In the present invention, it has been discovered that plasma miRNA-30d (SEQ ID NO: 1) is a novel biomarker that independently predicts response to CRT in patients with DHF. Moreover, miR-30d expression appears to correlate with wall stress and is released by primary CMs in EMVs.

Biomarkers of the Invention

The invention features biomarkers having at least 85% (e.g., 85%, 90%, 95%, 97%, 99%, or 100%) sequence identity to the sequence of miR-30d (SEQ ID NO: 1), miR-1254 (SEQ ID NO: 27), miR-142-5p (SEQ ID NO: 28), miR-766 (SEQ ID NO: 33), and miR-29c (SEQ ID NO: 29). Biomarkers of the invention can also include genes encoding proteins, particularly in pathways that are affected by changes in miR-30d, miR-1254, miR-142-5p, and miR-29c. Biomarkers of this nature include, but are not limited to, LIM and senescent cell antigen-like domains 1 (LIMS1), podocalyxin-like protein 1 (PODXL), Protein phosphatase 1 regulatory subunit 14c (PPP1R14c), mitogen-activated protein kinase kinase kinase 13 (MAP3K13), Janus kinase 1 (JAK1), (phosphatidyl glycerol phospholipase C (PGC1), calcium-calmodulin-dependent protein kinase type IV (CAMKIV), and mitogen-activated protein kinase kinase kinase kinase 4 (MAP4K4). The biomarkers of the invention may be used in the methods and kits as described below, to determine whether a patient might respond positively or poorly to a cardiac therapy such as CRT. The biomarkers of the invention may also be used to predict a patient's response to other cardiac therapies, e.g., miRNA based therapies, and to test the efficacy of cardiac therapies.

Methods for Predicting Response to Cardiac Therapies using Biomarkers of the Invention The invention features methods for predicting response to a cardiac therapy in a patient with HF before or after one or more cardiac therapy, by collecting a sample, e.g., a blood or plasma sample from a patient; measuring the level of expression of a biomarker, having at least 85% (e.g., 85%, 90%, 95%, 97%, 99%, or 100%) sequence identity to the sequence of miR-30d (SEQ ID NO: 1), miR-766 (SEQ ID NO:33), or miR1254 (SEQ ID NO: 27), in the sample, relative to a control sample; and making a prediction whether the patient will be responsive to a cardiac therapy. The method can be used to predict whether a patient, who suffered a heart failure, will respond positively to a cardiac therapy such as CRT or a miRNA based therapeutic.

A prediction of a positive response refers to a case where the HF symptoms will be alleviated and the risk of mortality will be reduced as a result of the cardiac therapy. For example a positive response can be an improvement in LV ejection fraction by >10% at 6 months post-therapy.

In the methods of predicting response to a cardiac therapy, the expression level of the biomarker can be determined relative to a control sample. A control sample can be a sample from a normal patient, or a sample from a patient who has undergone a cardiac therapy and has reduced symptoms after the therapy.

The methods of the invention can be used to predict whether a patient will be responsive to a cardiac therapy, for example an increase in the level of expression (e.g., an increase of 20%, 30%, 50%, 80%, 100%, 200%, 300%, 500%, 800%, 1000%) of the biomarker may indicate a positive response to a cardiac therapy, e.g. CRT. Alternatively, a decrease in the level of expression (e.g., a decrease of 20%, 30%, 50%, 80%, 100%, 200%, 300%, 500%, 800%, 1000%) of the biomarker may indicate a poor response to a cardiac therapy, e.g., CRT.

The methods of the invention can be used to predict a patient's response to CRT and classify the patient as a "responder", e.g., a patient with biomarker levels indicative of a positive response to CRT, or a "non-responder", e.g. a patient with biomarker levels indicative of a poor response to CRT (as shown in table 1).

TABLE 1

|  | Non-Responders (n = 7) | Responders (n = 7) |
| --- | --- | --- |
| Age | 52 +/− 9 | 55 +/− 9 |
| Male Gender (%) | 100 | 100 |
| Percent DCM | 100 | 100 |
| LBBB (%) | 83% | 83% |
| QRS duration | 130 | 160 |
| NYHA Baseline | 3 | 3 |
| LV lead position: lateral or posterolateral (%) | 100 | 100 |
| 6 month LVEF | 24 +/− 6 | 48 +/− 4 |
| LVEF change at 6 month | 1 +/− 7 | 19 +/− 4 |

Table 1 shows various data for patients who are classified as non-responders and responders to CRT.

The prediction can be made prior to a first cardiac therapy. Alternatively, the prediction can be made after the first cardiac therapy, or after a first cardiac therapy but before a second cardiac therapy. Furthermore, the prediction can be made at any time during the course of a cardiac therapy.

The methods of the invention may also include collecting nucleic acid molecules from a sample, e.g., a blood or a plasma sample from a patient. The methods of the invention may include amplifying the nucleic acid molecules using, e.g., polymerase chain reaction (PCR), to produce an amplified solution. The methods of the invention may further include performing qRT-PCR in a thermal cycler using the nucleic acid molecules collected from a sample or using the amplified solution described above to measure the level of expression of a biomarker in the sample. Procedures for performing qRT-PCR are described in, e.g., U.S. Pat. No. 7,101,663 and U.S. Patent Application Nos. 2006/0177837 and 2006/0088856, each of which is incorporated herein by reference.

Methods for Treatment of Cardiac Diseases using Biomarkers of the Invention

The invention features methods for the treatment of cardiac diseases, (e.g., HF) by collecting a sample, e.g. a blood or plasma sample, from a patient, measuring the level of expression of a biomarker, having at least 85% (e.g., 85%, 90%, 95%, 97%, 99%, or 100%) sequence identity to the sequence of miR-30d (SEQ ID NO: 1), miR-766 (SEQ ID NO:33), or miR1254 (SEQ ID NO: 27) relative to a control sample, making a prediction whether the patient will be responsive to a cardiac therapy, and if the prediction is positive, administering a cardiac therapy, e.g. CRT or a miR-30d therapy. In the method of the invention, a positive prediction is made when the level of the biomarker is increased relative to the control sample. For example, an increase in the level of expression (e.g., an increase of 20%, 30%, 50%, 80%, 100%, 200%, 300%, 500%, 800%, 1000%) of the biomarker may indicate a positive response to a cardiac therapy, and therefore warrant a cardiac therapy such as CRT. Alternatively, a decrease in the level of expression (e.g., a decrease of 20%, 30%, 50%, 80%, 100%, 200%, 300%, 500%, 800%, 1000%) of the biomarker may indicate a poor response to a cardiac therapy.

Cardiac Resynchronization Therapy for Cardiac Disease

For patients who meet clinical criteria for CRT, implantation of a device is well understood in the art. Typically, the device is implanted in the electrophysiology laboratory or operating room. An incision is made in the sub-clavicular region of the left or right shoulder, and a sub-cutaneous pocket is created by dissection. The cephalic and the subclavian veins are accessed either by cut-down or by the Seldinger technique and guiding sheaths are placed in the vein. A pacing lead is placed in the right atrial appendage via the guiding sheath and attached to the tissue via an active fixation mechanism. Similarly, a pacing and/or defibrillation lead is placed in the right ventricle and the fixation mechanism is deployed. Finally the coronary sinus is accessed using guiding wires and sheaths, and a coronary sinus pacing lead is placed in an appropriate branch via the sheath. All sheaths are removed and the leads are attached to a pacing/defibrillation generator and placed in the pocket. The pocket is then sutured close.

miRNA Based Therapy for Cardiac Disease

The invention also features a method of treating a cardiac disease by administering a therapeutic that targets a miRNA having at least 85% (e.g., 85%, 90%, 95%, 97%, 99%, or 100%) sequence identity to the sequence of miR-30d (SEQ ID NO: 1), miR-766 (SEQ ID NO:33), or miR1254 (SEQ ID NO: 27). The therapeutic can include a nucleic acid having at least 85% (e.g., 85%, 90%, 95%, 97%, 99%, or 100%) sequence identity to the sequence of SEQ ID NO: 1, SEQ ID NO:33, or SEQ ID NO: 27, or at least 85% (e.g., 85%, 90%, 95%, 97%, 99%, or 100%) sequence identity to the sequence of SEQ ID NO: 2, SEQ ID NO: 34, SEQ ID NO: 30. For example, the therapeutic can include a nucleic acid with the sequence of miRNA-30d. The therapeutic can also include a nucleic acid precursor for miRNA-30d, miRNA-1254, or miRNA-766 (e.g., a nucleic acid sequence encoding pre-miRNA-30d, pre-miRNA-1254, or pre-miRNA-766). The therapeutic can include a nucleic acid encoding either the precursor form, or the "mature" form of the miRNA cloned into an expression vector for delivery into tissue such that the miRNA is expressed by the expression vector inside the tissue. Alternatively, the therapeutic can include a compound (e.g., a drug or a peptide) that causes a change (e.g., an increase) in the level of expression of miRNA-30d, miRNA-1254, or miRNA-766 in a patient.

Construction of vectors for expression of nucleic acids (e.g., miRNA or pre-miRNA) for use in the invention may be accomplished using conventional techniques which do not require detailed explanation to one of ordinary skill in the art. For generation of efficient expression vectors, it is necessary to have regulatory sequences that control the expression of the miRNA. These regulatory sequences include promoter and enhancer sequences and are influenced by specific cellular factors that interact with these sequences, and are well known in the art.

The method of treatment using miRNA therapy can further include collecting a sample from a patient, e.g. a blood or plasma sample, and determining the level of expression of a biomarker, having at least 85% (e.g., 85%, 90%, 95%, 97%, 99%, or 100%) sequence identity to the sequence of SEQ ID NO: 1, SEQ ID NO: 33, or SEQ ID NO: 27, to monitor the treatment efficacy of the therapeutic that was administered to the patient.

Administration of miRNA Based Therapy

A variety of methods are available for the administration of miRNA based therapies, either for the delivery of the miRNA (or the precursor miRNA) or for the delivery of expression vectors that can express the miRNA (or the precursor miRNA) within tissue. These methods primarily focus on delivery of nucleic acids to tissue and include non-viral methods and viral methods.

Several non-viral methods exist for delivery of nucleic acids and expression vectors. For example, a colloidal dispersion system may be used for targeted delivery of nucleic acids. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 μm can encapsulate a substantial percentage of an aqueous buffer containing large macro molecules. RNA, DNA and even intact virions can be encapsulated within the aqueous interior and be delivered to cells in a biologically active form. For a liposome to be an efficient nucleic acid transfer vehicle, the following characteristics should be present: encapsulation of the nucleic acid (or expression vector) at high efficiency while not compromising their biological activity; preferential and substantial binding to a target cell in comparison to non-target cells; delivery of the aqueous contents of the vesicle to the target cell cytoplasm at high efficiency; and accurate and effective expression of genetic information.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization. The surface of the nucleic acid delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Additional methods are known in the art and are described, for example in U.S. Patent Application Publication No. 20060058255.

In one aspect of the invention, viral methods may be used for expression of miRNA in tissue. In this case, the expression vector encoding the miRNA or pre-miRNA sequence is encapsidated within a recombinant virus e.g., recombinant adeno-associated virus (AAV), recombinant retrovirus, recombinant lentivirus, recombinant poxvirus, recombinant rabies virus, recombinant pseudo-rabies virus, and recombinant herpes simplex virus, papovavirus, human immunideficiency virus (HIV), and adenovirus. These viruses are then applied to the subject (e.g., a patient) so that appropriate cells can be infected by these viruses and the miRNA can then be expressed in endothelial cells.

Preferred viruses include lentiviruses and adeno-associated viruses (AAVs). Both types of viruses can integrate into the genome without cell divisions, and both types have been tested in pre-clinical animal studies. Methods for preparation of AAVs are described in the art e.g., in U.S. Pat. No. 5,677,158, U.S. Pat. No. 6,309,634, and U.S. Pat. No. 6,683,058, each of which is incorporated herein by reference. Methods for preparation and in vivo administration of lentiviruses are described in US 20020037281 (incorporated herein by reference). Preferably, a lentivirus vector is a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding the fusion protein, an origin of second strand DNA synthesis and a 3' lentiviral LTR.

Retroviruses are most commonly used in human clinical trials, since they carry 7-8 kb and have the ability to infect cells and have their genetic material stably integrated into the host cell with high efficiency (see, e.g., WO 95/30761; WO 95/24929, each of which is incorporated herein by reference). Oncovirinae require at least one round of target cell proliferation for transfer and integration of exogenous nucleic acid sequences into the patient.

For use in human patients, the retrovirus will typically be replication defective. This prevents further generation of infectious retroviral particles in the target tissue. Instead the replication defective virus becomes a "captive" transgene stable incorporated into the target cell genome. Typically, in replication defective vectors, the gag, env, and pol genes have been deleted (along with most of the rest of the viral genome). Heterologous DNA (in case of the present invention, the sequence encoding the miRNA or pre-miRNA) is inserted in place of the deleted viral genes. The heterologous genes may be under the control of the endogenous heterologous promoter, another heterologous promoter active in the target cell, or the retroviral 5' LTR (the viral LTR is active in diverse tissues).

In one embodiment, the viruses are introduced into the body by intravascular injection. For localized targeting, virus injection from an IV catheter has already been used to achieve spatially discrete expression (e.g., of a single chamber of the heart).

Viruses encoding the miRNA or pre-miRNA may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Kit for Predicting Response to a Cardiac Therapy

The invention features a kit that includes reagents for collecting nucleic acids from a patient sample (e.g., blood sample or a plasma sample); reagents for amplifying the nucleic acid molecules to produce an amplified sample; and reagents for measuring the level of expression of a biomarker having at least 85% % (e.g., 85%, 90%, 95%, 97%, 99%, or 100%) sequence identity to the sequence of SEQ ID NO: 1, SEQ ID NO: 33, SEQ ID NO: 27. In one aspect, the kit includes reagents for measuring the level of expression of miR-30d (SEQ ID NO: 1), miR-766 (SEQ ID NO: 33), and miR-1254 (SEQ ID NO: 27). The kit may also include instructions for predicting response to a cardiac therapy, e.g., CRT based on the level of expression of the biomarker in the patient sample.

EXAMPLES

Example 1

Signature Pattern of miRNAs in "Responders" to CRT

Figure 2:
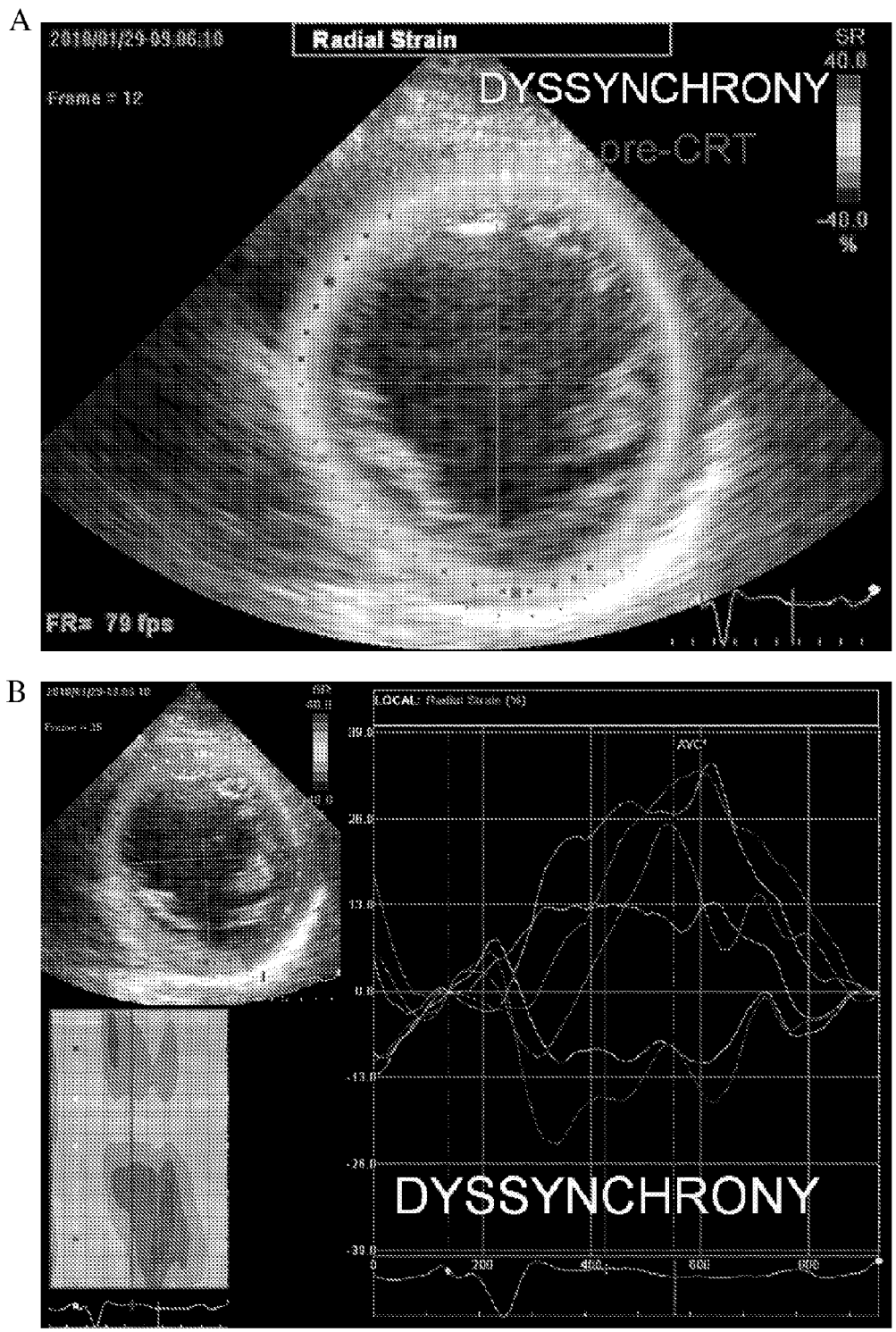
FIG. 2 is an image of an echocardiogram with superimposed strain patterns showing synchronized strain in a dyssynchronized strain/contraction in a patient with dyssynchronous heart failure.
Figure 3:
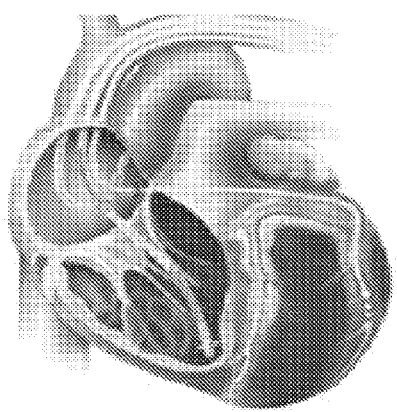
FIG. 3 is a schematic showing of where the leads are placed in cardiac resynchronization therapy.
Figure 3:
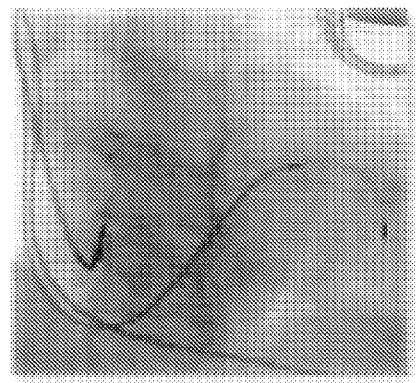
Figure 4:
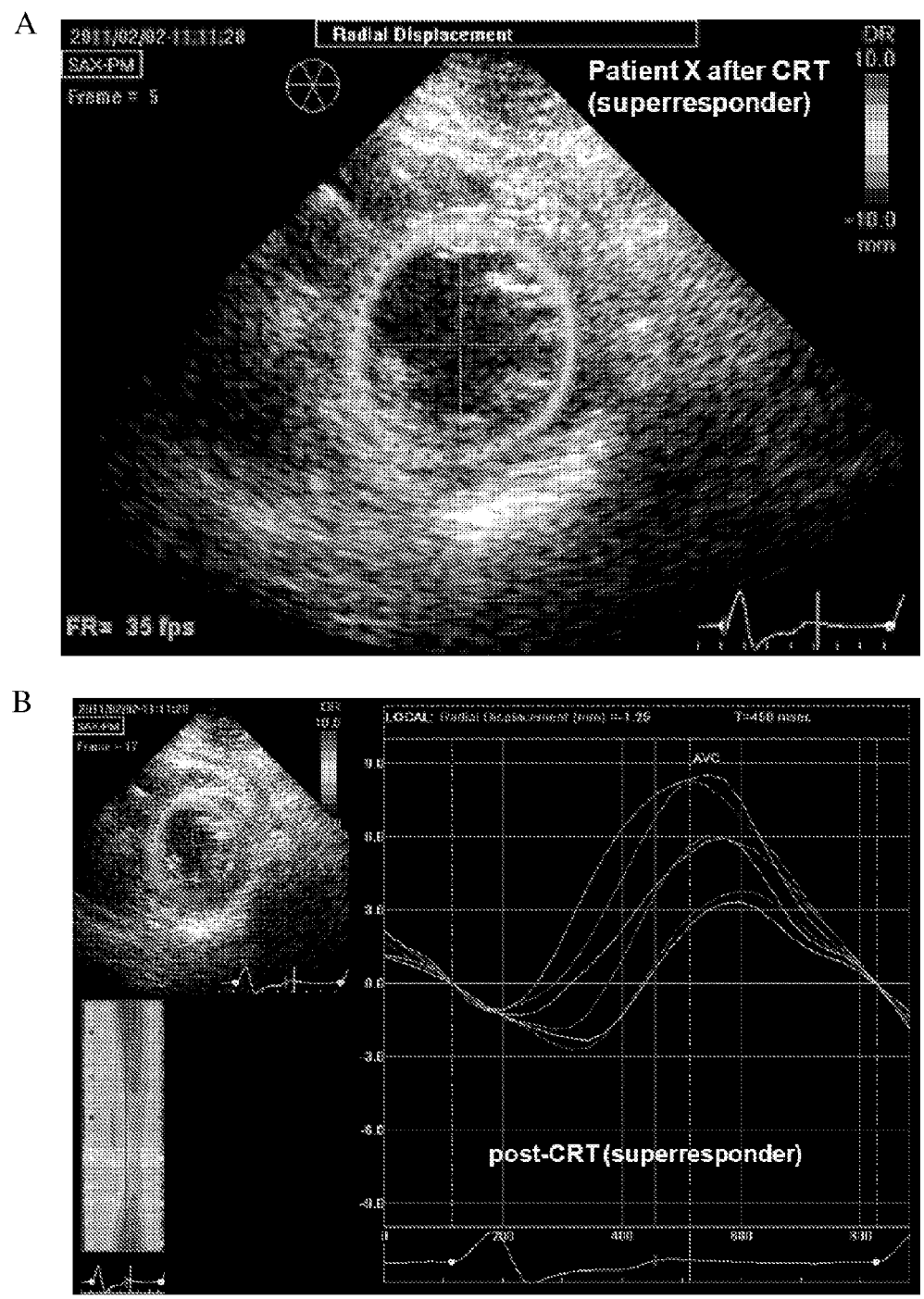
FIG. 4 is an image of an echocardiogram of a patient who has responded well to CRT with normalization of wall strain patterns and synchronous contraction.
Figure 5:
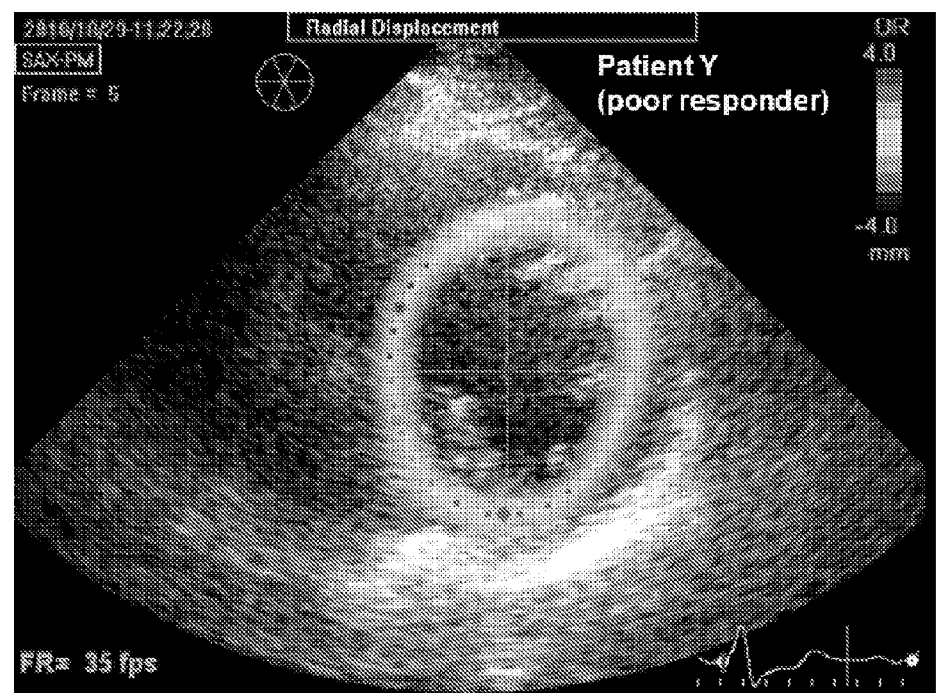
FIG. 5 is an image of an echocardiogram showing an example of a patient who did not respond to CRT and shows continued dyssynchrony and poor heart function.
Figure 5:
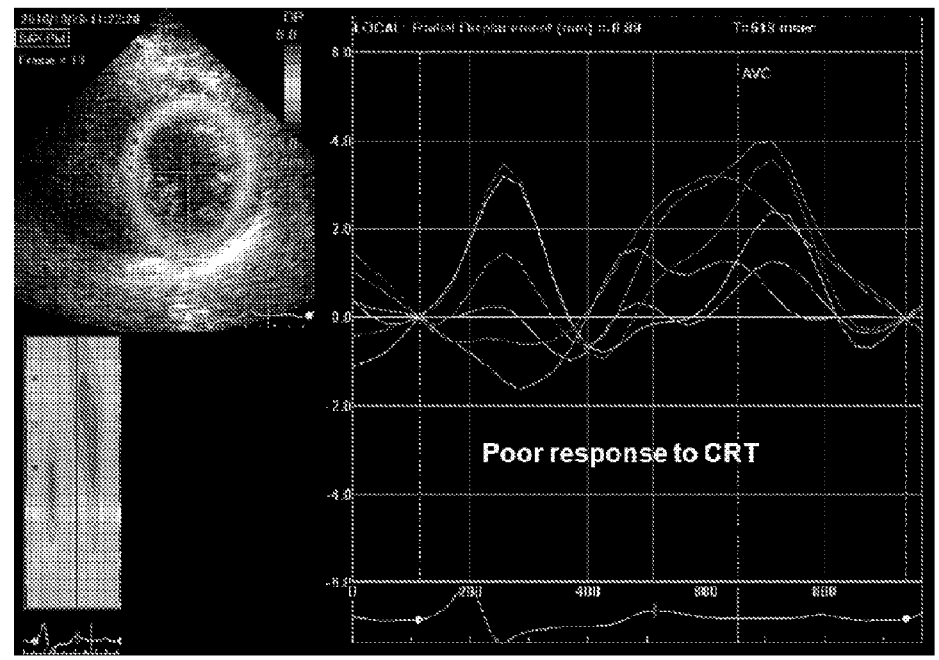
Figure 6:
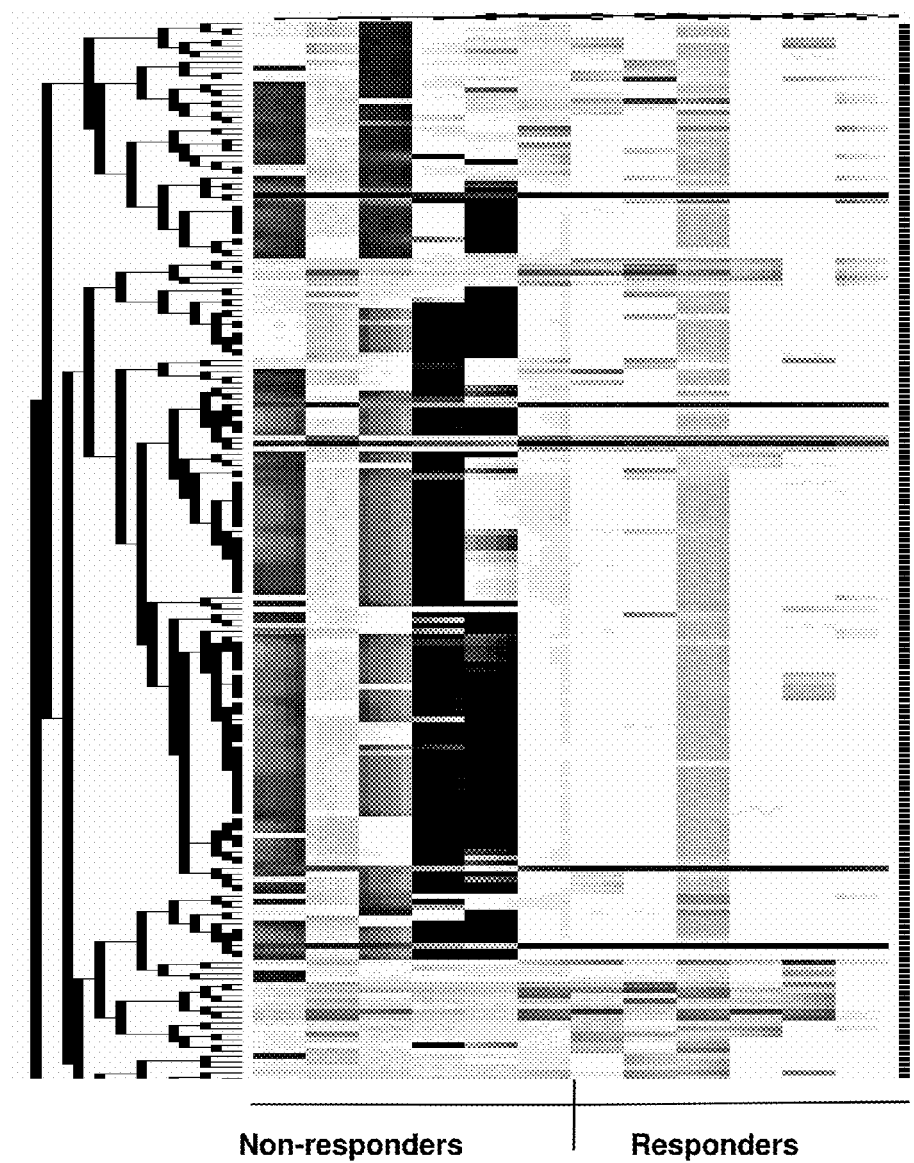
FIG. 6 is a graphical representation of all known miRNAs that are measured in 6 responders and 6 non-responders, subjected to hierarchical clustering. This graphic shows that the pattern of miRNAs in responders is different from non-responders.
Figure 7:
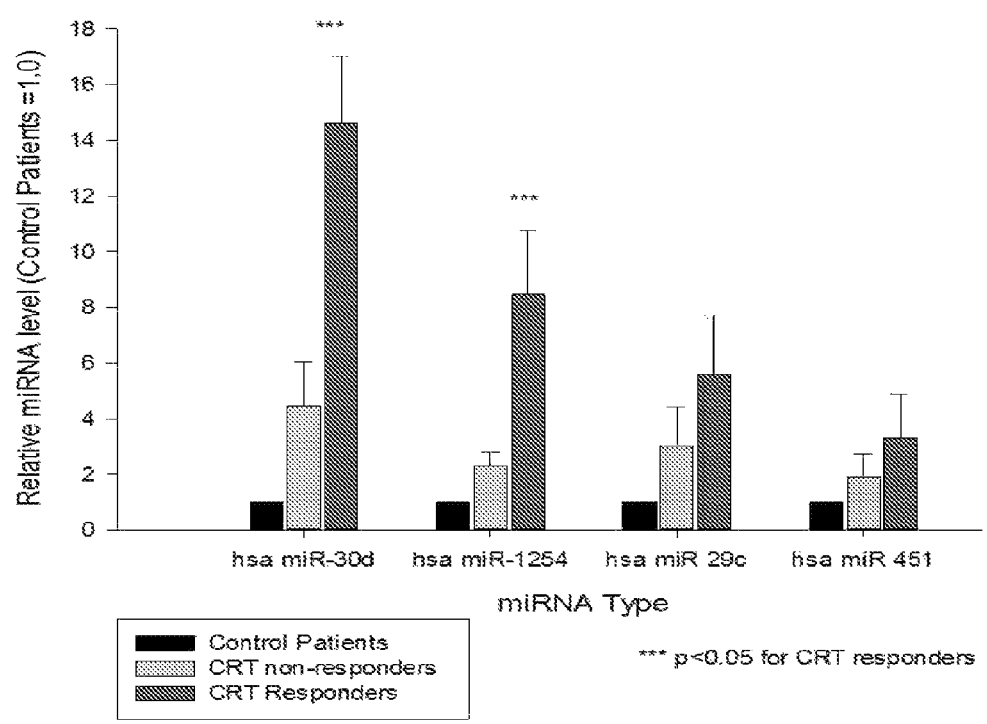
FIG. 7 is a graph showing qRT-PCR validation of miR-NAs discovered in a miRNA array. The graph shows a significant increase of miR-30d in 1254 patients who respond to CRT at 6 months.

Exemplary echocardigrams showing synchronized strain in a normal heart and dyssynchronous strain in a patient with HF are shown in FIGS. 1 and 2 respectively. The schematic in FIG. 3 shows how CRT is performed. FIGS. 4 and 5 are exemplary echocardiogram of responders and non-responders respectively. Human miRNAs were isolated from plasma (nirvana-PARIS, Ambion) obtained at baseline (prior to CRT implantation) from 6 responders and 6 non-responders to CRT (response was defined as improvement in LV ejection fraction>10% at 6 month follow-up). Patients were matched for age, gender, baseline LV function and co-morbidities. Screening of miRNA by qRT-PCR (Applied Biosystems), Taqman Human Microarray) revealed that the pattern of miRNAs in responders is different from non-responders (FIG. 6). Of all the miRNAs measured, 2 candidates were significantly different between the two groups. Validation of candidate miRNA in a prospective cohort of 62 patients undergoing CRT as well as 30 control patients with no heart failure and normal LV function revealed 4 candidates that were significantly different between control, non-responders and responders (FIG. 7). Candidate miRNAs were normalized to 'spike-in' C. elegans miR-39.

Example 2

Baseline Level of miR-30d Independently Predicts Response to CRT at 6 Months

Figure 8:
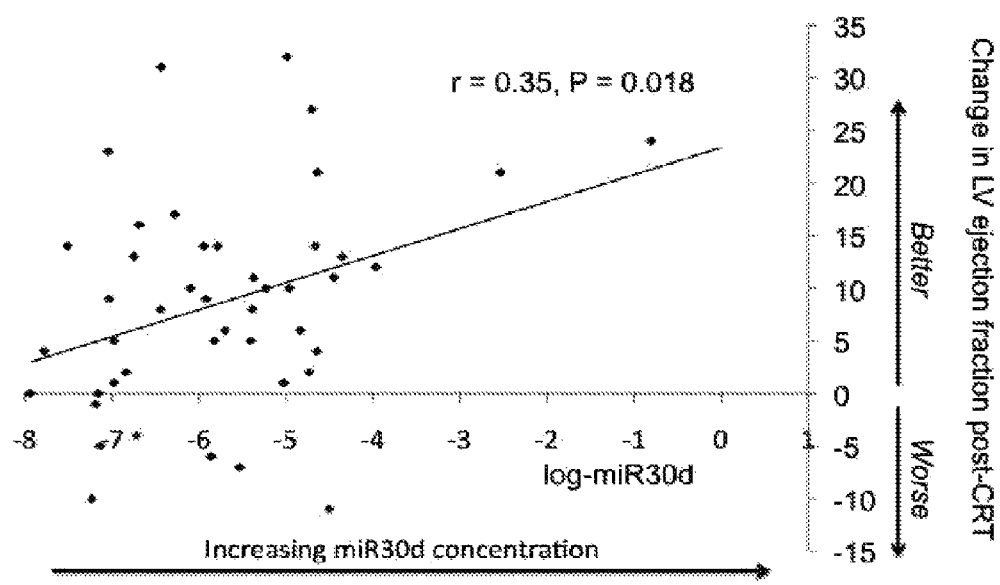
FIG. 8 is a graph showing that baseline levels of miR-30d correlate with increase in LVEF 6 months after CRT implant.
Figure 9:
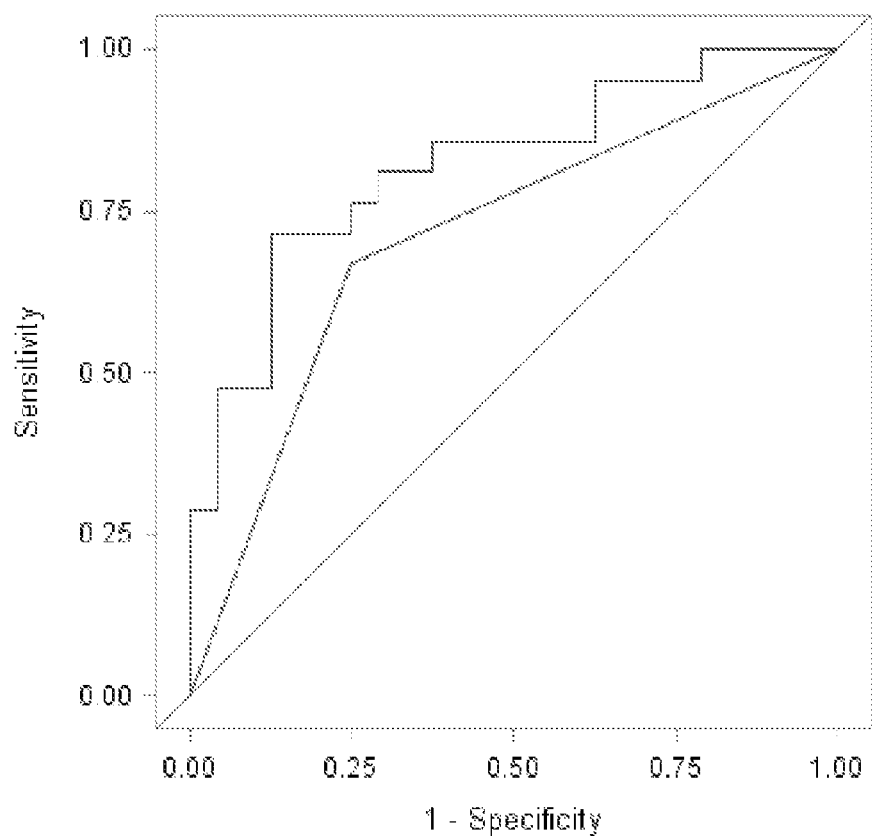
FIG. 9 is a graph showing a 'response operator curve' (ROC) comparing the best clinical predictor of responsiveness to CRT in our validation cohort of 45 patients with the curve representing incremental addition of miR-30d levels. This curve shows that addition of miR-30d improves the predictive power of the best available to predict response to CRT.

Multivariate regression models using miR-30d and clinical factors that were significantly different between responders and non-responders as explanatory variables demonstrated that miRNA-30d was an independent predictor of response to CRT. Notably, the level of miR-30d was linearly related to improvement in LV ejection fraction at 6 months after CRT (FIG. 8). 'Response operator curve' (ROC) comparing the best clinical predictor of responsiveness to CRT in the validation cohort of 45 patients with the curve representing incremental addition of miR-30d levels is shown in FIG. 9. This curve shows that addition of miR-30d improves the predictive power of the best available to predict response to CRT.

Figure 10:
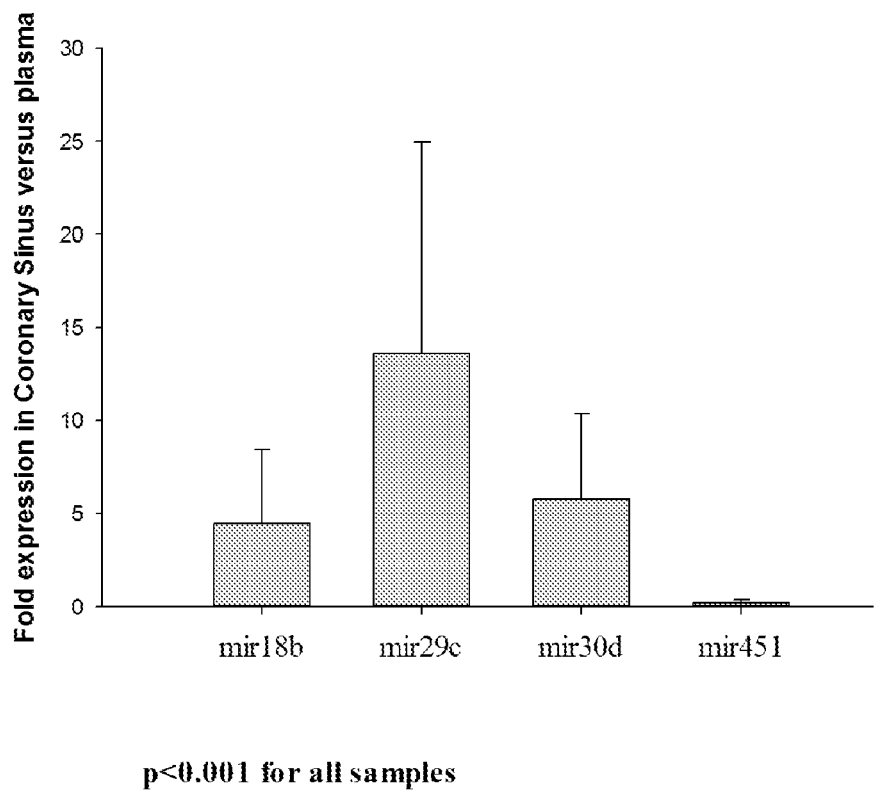
FIG. 10 is a graph showing that miR-30d is enriched in coronary sinus compared to peripheral blood.

Example 3 miR-30d is Enriched in the Coronary Sinus Compared to Peripheral Blood miRNAs were isolated from plasma obtained simultaneously from the coronary sinus and peripheral veins of patients undergoing CRT. qRT-PCR (Taqman, AB) for miR-30d (normalized to spike-in miR-39), showed that miR-30d was enriched in the coronary sinus compared to peripheral blood, suggesting a cardiac origin (FIG. 10).

Example 4 miR-30d is Increased in the Lateral Wall in Canine DHF

Figure 11:
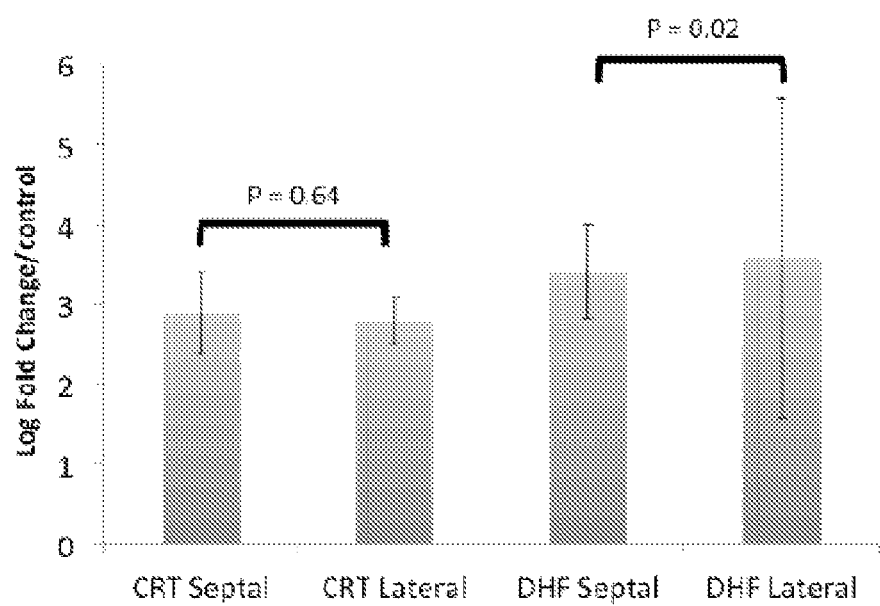
FIG. 11 is a graph showing expression of miR-30d in different tissues (as indicated), normalized to control septum.

Tissue was obtained from the lateral and anterior LV wall from control dogs and canine models of DHF and resynchronized (CRT) HF. miRNAs isolated using miRVana PARIS kit (Ambion), were subjected to qRT-PCR (AB-Taqman) for miR-30d, with U6 used as normalization control. miR-30d was significantly increased in DHF in both anterior and lateral walls, with a higher level noted in the lateral wall (FIG. 11) where wall stress is maximal. Resynchronization resulted in a reduction in miR-30d level, and normalization of the heterogeneity in miR-30d level between anterior and lateral wall in DHF.

Example 5

Endogenous miR-30d is Present in Primary CMs and is Enriched in EMVs

Figure 12:
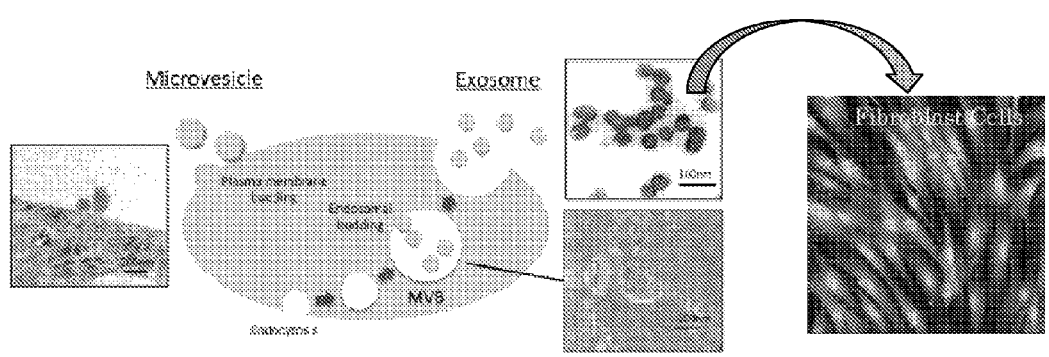
FIG. 12 is a schematic showing a proposed model for how circulating miR-30d works. miR-30d may get secreted from the heart cells and then alter protein expression in other cells to create a beneficial effect on the heart.
Figure 13:
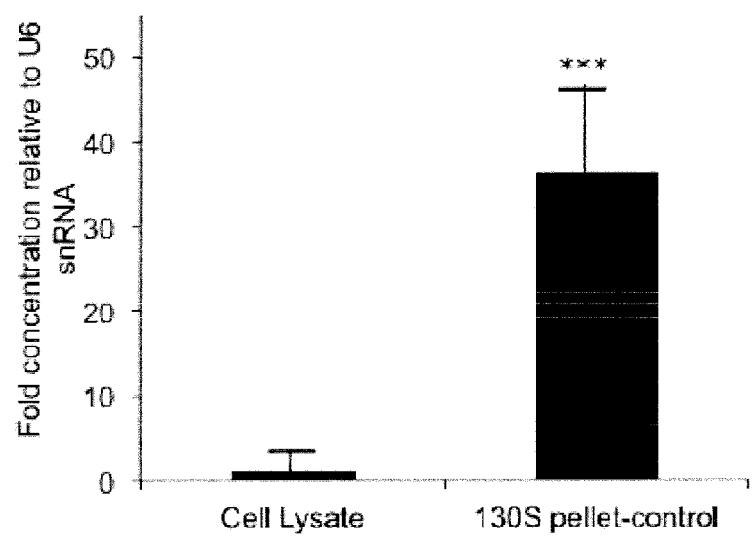
FIG. 13 is a graph showing enrichment of miR-30d in exosomes and microvesicles (termed 'EMV') compartment relative to cell-lysate.

A proposed model of how circulating miR-30d works is shown in FIG. 12. miR-30d may get secreted from the heart cells and then alter protein expression in other cells to create a beneficial effect on the heart. To test this model, miRNAs were isolated from primary rat neonatal CMs after 5 days in culture, and subjected to qRT-PCR (Taqman, AB) with miR 30 Taqman assay. miR-30d expression was detected both in CMs as well as cardiac fibroblasts. EMVs were purified from culture medium by ultracentrifugation as described. RNA in the EMV fraction was isolated as above and subjected to QRT-PCR assay for miR-30d as described above, with U6 serving as a control. There was a marked enrichment of miR-30d in the EMV compartment (FIG. 13), suggesting that miR-30d is packaged and released from CMs.

Example 6

Figure 14:
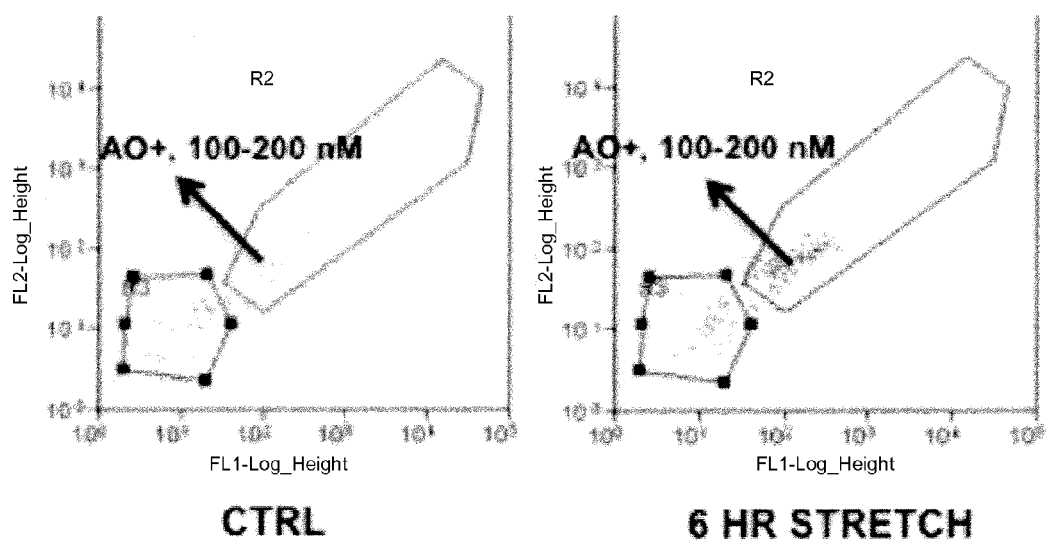
FIG. 14 is a graph showing the results of fluorescence assorted cell sorting (done by size and fluorescence gating) performed on purified EMVs from cardiomyocyte (CM)-conditioned medium. An increase in RNA-containing EMVs is observed following pathological stretch for 6 hours.

Primary CMs Subjected to Pathological Rotational Stress Increase Release of EMVs A model system of pathological hypertrophy in primary CMs subjected to rotational stretch was developed. CMs subjected to 6 hours of stretch have a gene expression profile consistent with pathological hypertrophy, with an increase in mRNA for atrial natriuretic peptide (ANP) and beta-myosin heavy chain (B-MHC). Culture medium was collected from CMs subjected to rotational stress or from non-stretched CMs (CTRL). Medium was subjected to ultracentrifugation as in C2.1 to isolate EMVs. EMVs were stained with Acridine Orange (to label RNA and DNA content), and subjected to FACS at wavelength 525 nm with gating based on both size and fluorescence. Results suggested an increase in AO-positive, 100-200 nM sized particles in the stretched CMs (FIG. 14).

Example 7

Over-Expression of miR-30d in CMs Increases Causes Cellular Hypertrophy

Figure 15:
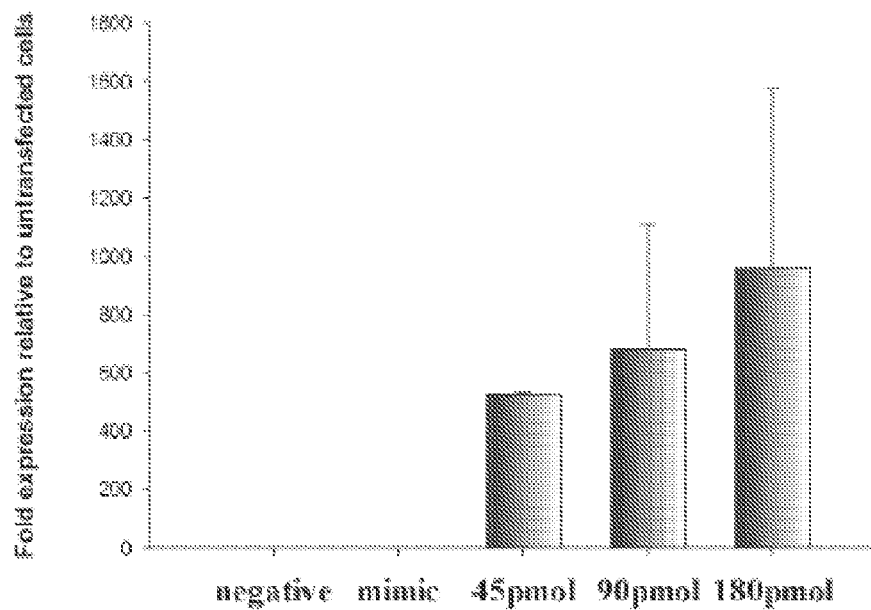
FIG. 15A is a graph showing that transfection of pre-miR30d into primary CMs causes increase in miR-30d levels.
FIG. 15B is a graph showing that transfection of pre-miR30d into primary CMs causes increase in cell growth.
Figure 15:
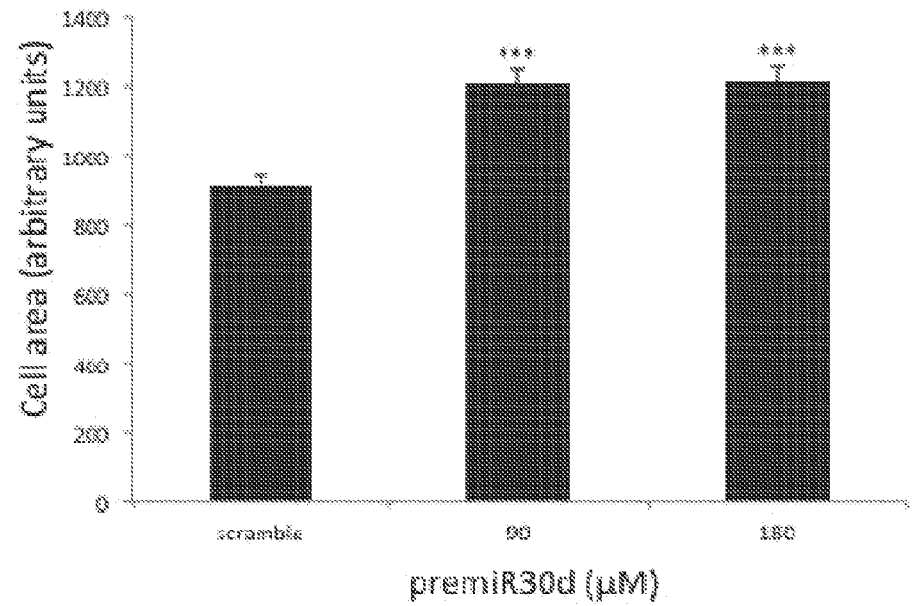

Pre-miRNA-30d (Applied Biosystems) was transfected into primary CMs using lipofectamine (Invitrogen) at different concentrations. qRT-PCR of RNA isolated from CMs after 48 hours showed a dose-dependent increase in miR-30d expression, as well as some degree of hypertrophy (FIG. 15), suggesting a biological effect of the transfected miRNA.

Figure 16:
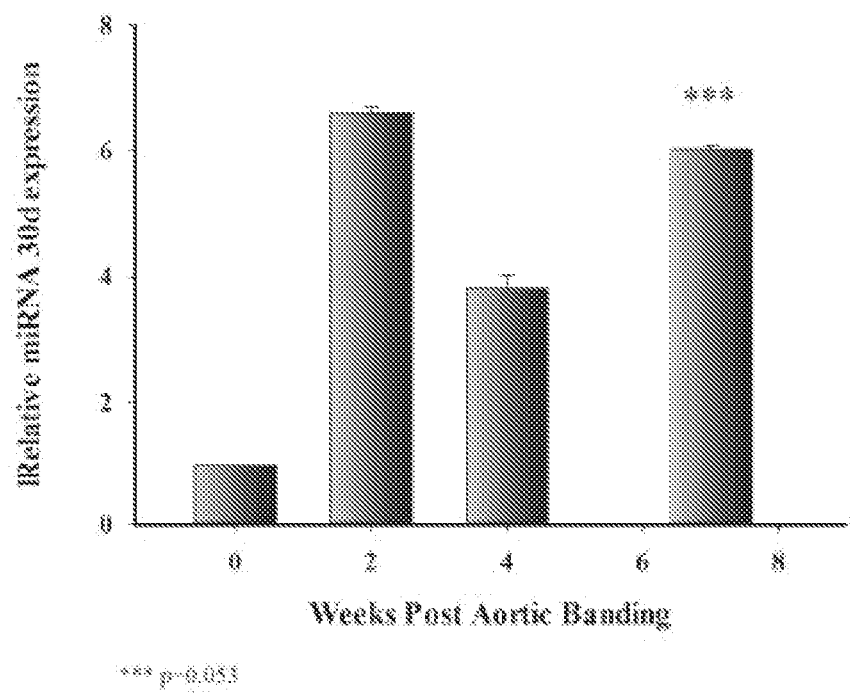
FIG. 16 is a graph showing that miR-30d levels increase rapidly after transverse aortic constriction (TAC) and stay elevated during adaptive hypertrophy stage.

Example 8 miR-30 d Levels Increase in the Hypertrophy Phase After Transverse Aortic Constriction (TAC) in Mice C57/BL6 12 week old male mice were subjected to (TAC) and followed with serial echocardiograms and terminal MRIs at 2, 4 and 7 weeks. MRI showed cardiac cellular hypertrophy without significant fibrosis at these time points. qRT-PCR using miRNAs isolated at these time points showed a trend towards increased miR-30d (although statistical significance was not reached likely due to small sample size) (FIG. 16).

Example 9

Experimental Methods

Human Patient Data and Serum Samples

Fifty-two (12 for initial discovery and 40 for validation) consecutive patients referred for CRT pacemaker implantation for clinical indications (class II-IV heart failure with LV ejection fraction<35% and QRS duration>120 msec with left bundle branch block or paced QRS morphology) were studied. Clinical and demographic characteristics were abstracted from the electronic medical record for pre-implant and post-implant heart failure status and echocardiographic data. Transthoracic echocardiography was performed for clinical indications before and after CRT pacemaker implantation, and LV ejection fraction and dimensions were calculated by either single dimension method or method of discs at the discretion of the interpreter.

Samples of peripheral venous and coronary sinus blood were collected at the time of CRT pacemaker implantation and peripheral plasma prepared.

Control sera were also obtained from a cohort of 29 patients referred for the evaluation of dyspnea at a cardiopulmonary exercise testing lab (Massachusetts General Hospital, Boston, Mass.) and subsequently found to have non-cardiac etiology for dyspnea.

Human Plasma RNA Extraction

Blood from patients undergoing CRT pacemaker implantation was collected at the time of device placement. Plasma was prepared from the samples and frozen at −80° C. At the time of RNA extraction, plasma samples were thawed on ice and 50 pmol of C. Elegans miRNA (cel-miR 39, Ambion, Inc.) was added as a spike-in control. mRNA and miRNA were extracted using the mirVANA PARIS RNA isolation kit (Ambion, Inc., Grand Island, N.Y.) and samples were promptly frozen at −80° C.

Taqman Microarray Screening

Screening of six patients without change in ejection fraction (mean change in EF 1%) and six patients with a robust change in ejection fraction (mean EF increase 24% at 6 months) was performed using the Megaplex miRNA primer pool (Applied Biosystems, Foster City, Calif.). Briefly, human samples prepared as above were reverse transcribed using a pool of stem-looped primers designed to amplify a total of 766 different miRNAs. The pool of reverse transcribed RNA was subjected to quantitative PCR (qPCR) on a pair of low density arrays containing 383 miRNA species each. The results were analyzed using non-hierarchical clustering to look for miRNAs that differed significantly between the groups.

Canine Cardiac Sample Preparation

In the canine model of dyssynchronous heart failure (DHF) and CRT, adult mongrel dogs (Bruce Rotz Kennels, Shippensberg, Pa.) underwent left bundle branch ablation followed by either six weeks of rapid atrial pacing (200 beats per min) to induce DHF, or three weeks of rapid atrial pacing followed by three weeks of biventricular pacing at the same rate (CRT). At terminal study, dogs were anaesthetized and samples collected as previously described. 50-100 mg aliquots from the septal and lateral walls of each dog's left ventricle were used for experiments.

At the time of experiment, tissue samples were thawed on ice, weighed, and then placed in either a guanidinium hydrochloride-containing solution (Cell disruption buffer, Ambion Inc.) for RNA extraction, or 1× cell lysis buffer (Cell Signaling) containing 1× phosphatase inhibitor (Thermo Scientific), 1× protease inhibitor (Calbiochem) and 1 mM phenylmethanesulfonyl fluoride (Cell Signaling), for Western blot analysis. Tissue was mechanically disrupted for 5 minutes by a 5 mm steel bead (Qiagen, Inc., Valencia, Calif.) using the Qiagen TissueLyzer LT disruptor at 5 Hz. Following disruption, RNA was extracted using the mirVANA PARIS kit according to manufacturer's protocol. Protein samples were lysed for 1 hr, sonicated, and centrifuged at 10,000 g for 5 min. An aliquot of the resulting supernatant, containing 50 µg protein, was incubated with 1× SDS-Sample buffer (Boston BioProducts) at 65° C. for 5 min.

Neonatal Rat Ventricular Myocyte Transfection, Treatment, and Fixation

Neonatal rat ventricular cardiomyocytes were harvested and prepared from 1 day postnatal Sprague-Dawley rats as previously described. Cardiomyocytes were cultured in serum-free, antibiotic-free DMEM (Gibco). Forty-eight hours after plating, cells were transfected using Lipofectamine 2000 (Invitrogen Inc.) with miR-30d (90 pmol/mL; Ambion Inc.) or a negative control mimic (Ambion Inc.). Cells were harvested by mechanical scraping 48 h after transfection and RNA was isolated using the miRVANA PARIS RNA isolation kit (Ambion). Alternatively, cells were lysed in protein lysis buffer and prepared for Western blot analysis as described above.

For hypertrophy imaging, 48 h after transfection, cells were fixed in 4% Paraformaldehyde (PFA) for 5 min, followed by permeabilation by 0.5% Triton-X 100 in PBS for 5 min. Cells were then washed twice in PBS and blocked for 1 h at RT in 5% BSA in PBS. Cells were incubated with sarcomeric alpha actinin antibody (1:500, 5% BSA in PBS, Sigma) for 1 h, washed three times for 5 min each in PBS and incubated in the dark with anti-mouse 488 secondary antibody (1:500, 5% BSA in PBS, Invitrogen). Finally, cells were washed three times for 5 min each in PBS and mounted with hard-set DAPI mounting media. Cells were imaged the following day using a Zeiss upright confocal microscope and cell size was analysed using ImageJ software.

TNF-α treatment was performed by adding TNF-α to a final concentration of 25 ng/mL for 24 hours. Cells were harvested by mechanical scraping followed by RNA extraction as described above. Alternatively, an apoptosis assay was performed on TNF-α-treated cells using the cell death detection ELISAPLUS kit (Roche) according to manufacturer's protocol.

Mechanical Stretch

Mechanical stretch of cardiomyocytes was performed using previously described apparatus developed. In brief, cardiomyocytes were cultured on a silicone membrane and subjected to 20% stretch for 6 hrs at 3 Hz. The culture media was then collected and exosomes and microvesicles (EMVs) were isolated using multiple centrifugation steps as previously described. The isolated fraction was incubated with 20 µm/L acridine orange for 90 min at room temperature protected from light. Exosomes and microvesicles were pelleted by ultracentrifugation at 100,000 g for 2 hr and washed with PBS to remove excess acridine orange. This was repeated twice. The final pellet was re-suspended in 1 mL PBS and sorted based on size (<200 nm) and fluorescence using the Propel Lab's Nano-View forward scatter detector integrated onto a Beckman Coulter MoFlo XDP cell sorter. Sorted samples were re-pelleted as described above and RNA was extracted using the miRVANA PARIS RNA isolation kit (Ambion).

Reverse Transcription-Quantitative PCR (RT-PCR)

RT-PCR of individual candidate miRNAs was performed using the TaqMan qRT PCR kit. (Invitrogen, Inc.). Briefly, for each miRNA, a specific hairpin primer was used for reverse transcription to a DNA product amenable to amplification in quantitative PCR (qPCR) utilizing FAM-3 fluorescence detection on an Applied Biosystems 7900 HT Fast Real-Time PCR system (Foster City, Calif.). Primers were ordered from Ambion, Inc (Taqman miRNA assays). For each serum sample, qPCR was performed for the candidate miRNA as well as for the spike-in control. The number of cycles to reach threshold for a given sample relative to the spike-in control is related to the relative concentration of the candidate miRNA ($\Delta C_t^{miRNA} - \Delta C_t^{cel-miR\ 39}$). The difference of $\Delta C_t$ values between any two samples is subsequently exponentiated to generate the relative fold-change between the samples (see Statistical analysis, below). miR-30d concentrations in canine cardiac samples and cultured cardiomyocytes were determined relative to U6 snRNA as a housekeeping gene.

Reverse transcription of non-miRNA RNA species was performed using the multiscribe reverse transcription kit (Clontech Inc). Briefly, 1 µg of extracted RNA was used in an RT reaction using a 10× random priming mix to generate cDNA. qPCR was performed using the iQ SYBR Green Supermix (Bio-Rad Inc., Hercules Calif.) on a CFX384 real-time PCR system. Concentrations of all miRNAs were determined relative to GAPDH. Primers used were as follows:

```
GAPDH
                                            (SEQ ID NO: 3)
forward 5'-AAC TCC CTC AAG ATT GTCAGC AA-3', (SEQ ID NO: 4)
reverse 5'-GGC TAA GCA GTT GGT GGT GC-3';
ANP
                                            (SEQ ID NO: 5)
forward 5'-AAG AAC CTG CTA GAC CAC CTG G-3', (SEQ ID NO: 6)
reverse 5'-GCT TCC TCA GTC TGCTCA CTC A-3';
α-MHC
                                            (SEQ ID NO: 7)
forward 5'-CCG AGT CCC AGG TCA ACA AG-3', (SEQ ID NO: 8)
reverse 5'-TCA TCG TGC ATT TTC TGC TTG G-3';
β-MHC
                                            (SEQ ID NO: 9)
forward 5'-GAG AGA TGGCTG CAT TTG GG-3', (SEQ ID NO: 10)
reverse 5'-GTC ACC GTC TTG CCA TTC TC-3';
MAP4K4
                                           (SEQ ID NO: 11)
forward 5'-GCC TTA TGG GGA GTG AAT TT-3', (SEQ ID NO: 12)
reverse 5'-ACC CCT GCT TCTTCT CAA CT-3';
lims1
                                           (SEQ ID NO: 13)
forward 5'-CAA CTG CGG GAA GGA GCT AA-3', (SEQ ID NO: 14)
reverse 5'-GGC ATT CAC TAC TCG CCC TT-3';
JAK1
                                           (SEQ ID NO: 15)
forward 5'-AGG CAA GAG TGCATA GAG CG-3', (SEQ ID NO: 16)
reverse 5'-GGG TCT TGT CCT TGA GTG GG-3';
PGC1
                                           (SEQ ID NO: 17)
forward 5'-GTA GGC CCA GGT ATG ACA GC-3', (SEQ ID NO: 18)
reverse 5'-CTC TCT GCG GTA TTCGTC CC-3';
CamKIV
                                           (SEQ ID NO: 19)
forward 5'-GAC TTC AAT CAA AGG CGG CG-3', (SEQ ID NO: 20)
reverse 5'-GAG GAT CCC GTT TAG AGC CG-3';
PPPIR14C
                                           (SEQ ID NO: 21)
forward 5'-GCT CCT CAA GGGAGG ATT CG-3', (SEQ ID NO: 22)
reverse 5'-TTT CTT CTT CCT CGC AGC CA-3';
MAP3K13
                                           (SEQ ID NO: 23)
forward 5'-ACA GAC GTG GCA GAG TAA GC-3', (SEQ ID NO: 24)
reverse 5'-CTG CAG AGG CAATGT CCA GA-3';
PODXL
                                           (SEQ ID NO: 25)
forward 5'-ATC CTG CCA TAA AGC CCC AC-3', (SEQ ID NO: 26)
Reverse 5'-AGG GCT CCC CTT ACA AAA GC-3'.
```

Western Blotting

Samples were separated using SDS-PAGE on a Criterion TGX 4-20% gel (Bio Rad), and transferred to nitrocellulose membrane (Bio Rad). Membranes were probed overnight with specific primary antibodies. All antibodies were purchased from Cell Signaling with the exception of the MAP4K4 antibody, which was purchased from LifeSpan BioSciences Inc. Secondary antibody against rabbit IgG conjugated with horse raddish peroxidase was used for detection (Dako, Denmark). Membranes were developed using super signal west pico chemiluminescent substrate and super signal west femto maximum sensitivity substrate (Thermo scientific), and imaged on a Chemidock MP imaging system (Bio-Rad). Where multiple proteins of similar size were analysed, membranes were stripped by incubation with stripping buffer (0.76 g Tris, 2 g SDS, 700 µl β-mercaptoethanol in 100 ml) for 40 min, and re-probed with the primary antibody of interest.

Statistical Methods

Baseline clinical and demographic variables were compared by a Student's t-test or Kruskal Wallis non-parametric testing (depending on data normality for continuous data) or Fisher exact testing (for categorical data). For identification of association between clinical, echocardiographic, and miR concentrations and outcome, a CRT "responder" was defined as an increase in LV ejection fraction≥10% between baseline and follow-up transthoracic echocardiography after CRT pacemaker implantation. Univariable logistic regression analysis for association with "CRT responder" status was performed, including age, gender, etiology of heart failure, pre-implant QRS, medication use, baseline LVEF and LV dimensions, and selected miRNA concentrations (log-transformed). A parsimonious stepwise multivariable logistic regression model was constructed for association with CRT responder status (using $P<0.15$ for model entry and $P<0.05$ for model retention), including all covariates in univariable logistic regression.

Figure 17:
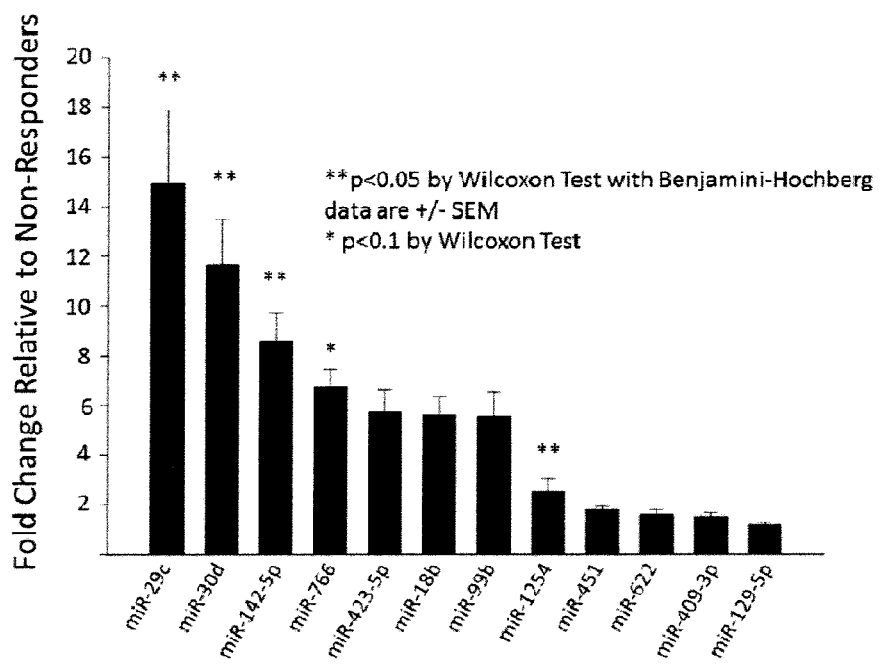
FIG. 17A is a graph showing the change of different miRNAs relative to non-responders.
FIG. 17B are graphs showing concentrations of particular miRNAs in control, non-responder, and responder populations.
Figure 17:
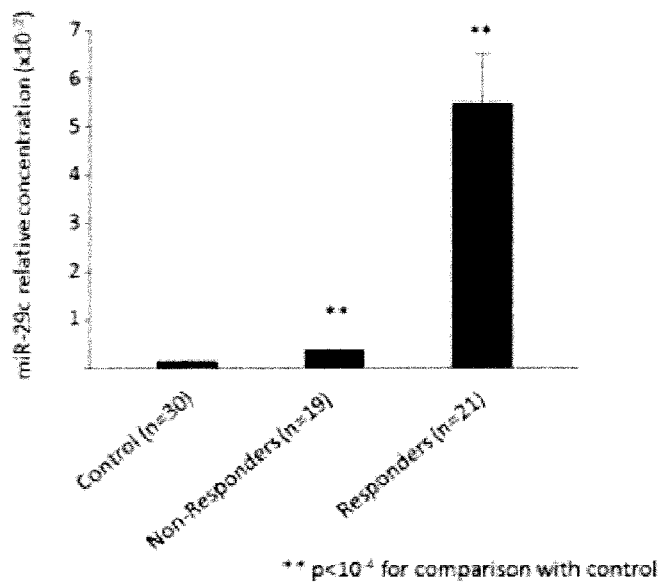

For miRNA analysis, CT values from responder, non-responder, and volunteer (non-HF) population were averaged. To determine the relative fold difference between responders and non-responders (FIG. 17a), the difference in CT values between responders and non-responders was exponentiated (base 2) to generate fold change. To determine differences between selected miRNAs between volunteers versus non-responder or responder population, the difference in CT values between each HF group (responder or non-responder) and the volunteer population were exponentiated (base 2) to generate fold difference (FIG. 17B). In this case, volunteer fold difference values were unity (referent). A pooled standard error of measurement for each comparison (volunteer vs. non-responder; volunteer vs. responder) was calculated as the square root of the sum of squares of standard deviation in CT value in each group, divided by the number of individuals in each group. Differences in miRNA concentrations between group (volunteer vs. non-responder; volunteer vs. responder) were evaluated using an unpaired Student's t-test of average CT values in each group. Given the exploratory nature of this analysis to identify the greatest number of candidate biomarkers, correction for multiple hypothesis testing was not performed.

A two-sided P value<0.05 was considered significant for all analyses. All statistical analyses were performed using SAS 9.3 (SAS Institute, Cary, N.C.).

Example 10

Taqman Microarray Screening Results

From the initial cohort of 52 patients, the six patients who had the greatest increase in ejection fraction (EF) and 6 patients with no change in EF at six months after CRT implantation were chosen. Characteristics of this cohort are shown in Table 1. The plasma of heart failure patients receiving CRT were screened using a microarray approach. To improve the sensitivity of the screen, only patients who had non-ischemic cardiomyopathies and left bundle branch block were chosen. The patients were screened using the Taqman miRNA array to look at expression levels of 766 known human miRNA species in serum. A number of miRNA species that differed between the CRT responders and non-responders were identified, and these levels were also significantly different from non-heart failure patients. It was found that four miRNA species, miR-409-3p, miR-30d, miR-99b, and miR-766 were significantly different in the responder group (p<0.05); miR-142-5p was close to meeting statistical significance (p=0.0582), when analyzed with a 5% false discovery rate by the Benjamini-Hochberg method. The patient characteristics and miRNA data has been deposited in the NOH-GEO database. One of these, miR-30d, was an independent predictor of CRT response in a multivariate model incorporating multiple clinical variables. When compared to current clinical criteria that are used to select patients for CRT placement, this miRNA alone provides as much discriminatory power in the cohort.

Example 11

Validation Cohort

The results were validated in the 40 remaining patients in the cohort with LBBB who met guideline criteria for CRT. Baseline levels of the plasma miRNAs identified in the 'discovery cohort' were analyzed in this prospective cohort that were followed for at least six months following their CRT implantation. CRT 'response' was defined by an increase in LVEF≥10% at six months after implant. Patient characteristics of this cohort, stratified by CRT "responder" (N=21; 53%) or "non-responder" (N=19; 48%) status are shown in Table 2. The mean age for the entire cohort was 67±13 years (20% female, 65% ischemic HF). The average LVEF before CRT implantation was 24.9±6.2% with average pre-CRT QRS duration 174±27 msec. There was a trend toward more frequent prior revascularization in non-responders (68% vs. 33% in responders; P=0.06), but disease severity (as reflected by renal function, QRS duration, baseline NYHA class and baseline LVEF) was similar between responders and non-responders.

The five miRNA species identified as different between responders and non-responders were measured retrospectively in the 'discovery cohort' (409-3p, 30d, 99b, 766 and 142-5p, as well as miR-451) in the baseline pre-implant peripheral plasma from the validation cohort. In addition levels of six additional miRNAs (miR-409-3p, miR-1254, miR-129-5p, miR-18b, miR-622, and miR-29c), which have been reported to be differentially expressed in patients with HF compared with control patients were also measured. It was found that miR-30d, miR-1254, miR-142-5p, and miR-29c were significantly different between the two groups ($p<0.05$ by Wilcoxon Rank Sum test with Benjamini-Hochberg correction for 5% false discovery rate) (FIG. 17A).

The levels of these four miRNA species were compared with serum levels in a cohort of patients who had been referred for cardiopulmonary exercise testing for the evaluation of dyspnea, and who had been found to have no detectable intrinsic cardiac disease (referred to as control cohort). The four panels in FIG. 17B show that the levels of each of these miRNA species are significantly elevated in the HF patients (both responders and non-responders) compared to the control cohort.

TABLE 2

Baseline demographic, echocardiographic and biochemical characteristics of the study population stratified by response to CRT. P values represent comparison between responder and non-responder population.

| Covariate | All (N = 40) | Non-responder (N = 19) | Responder (N = 21) | P value |
|---|---|---|---|---|
| Age, years | 67.1 ± 13.2 | 68.7 ± 12.9 | 65.8 ± 13.6 | .50 |
| Female gender, n (%) | 8 (20%) | 2 (10%) | 6 (29%) | .24 |
| Ischemic HF etiology, n (%) | 26 (65%) | 15 (79%) | 11 (52%) | .10 |
| Serum creatinine, mg/dl | 1.44 ± 0.48 | 1.48 ± 0.52 | 1.40 ± 0.47 | .82 |
| Prior revascularization, n (%) | 20 (50%) | 13 (68%) | 7 (33%) | .06 |
| Baseline NYHA class | 3.0 ± 0.3 | 3.0 ± 0.4 | 3.0 ± 0.3 | .98 |
| QRS duration on implant, msec | 174 ± 27 | 172 ± 29 | 175 ± 26 | .75 |
| Bundle Branch Block, n (%) | | | | .10 |
| LBBB | 25 (63%) | 9 (47%) | 16 (76%) | |
| Paced | 15 (37%) | 10 (53%) | 5 (24%) | |
| Atrial fibrillation, n (%) | 13 (33%) | 6 (32%) | 7 (33%) | 1 |
| Diabetes mellitus, n (%) | 13 (33%) | 6 (32%) | 7 (33%) | 1 |
| Hypertension, n (%) | 24 (60%) | 13 (68%) | 11 (52%) | .35 |
| Medication use, n (%) | | | | |
| ACE inhibitor | 23 (58%) | 13 (68%) | 10 (48%) | .22 |
| ARB antagonist | 12 (30%) | 4 (21%) | 8 (38%) | .31 |
| Aldosterone antagonist | 14 (36%) | 5 (26%) | 9 (43%) | .33 |
| Beta-blocker | 37 (93%) | 18 (95%) | 19 (90%) | 1 |
| Digoxin | 8 (20%) | 6 (32%) | 2 (10%) | .12 |

TABLE 2-continued

Baseline demographic, echocardiographic and biochemical characteristics of the study population stratified by response to CRT. P values represent comparison between responder and non-responder population.

| Covariate | All (N = 40) | Non-responder (N = 19) | Responder (N = 21) | P value |
|---|---|---|---|---|
| Diuretics | 32 (80%) | 16 (84%) | 16 (76%) | .70 |
| Transvenous implant, n (%) | 38 (95%) | 19 (100%) | 19 (90%) | .49 |
| Baseline echocardiography | | | | |
| LV ejection fraction, % | 24.9 ± 6.2 | 25.9 ± 6.4 | 24.0 ± 6.1 | .36 |
| LV end-diastolic dimension, mm | 62.1 ± 8.3 | 61.6 ± 8.0 | 62.6 ± 8.7 | .72 |
| LV end-systolic dimension, mm | 53.4 ± 8.5 | 52.4 ± 8.3 | 54.7 ± 8.8 | .44 |
| Follow-up echocardiography | | | | |
| Days to echo follow-up | 285 ± 114 | 282 ± 87 | 288 ± 137 | .74 |
| LV ejection fraction, % | 34.8 ± 10.4 | 27.8 ± 6.6 | 41.1 ± 9.2 | <.0001 |
| LV end-diastolic dimension, mm | 58.1 ± 9.5 | 60.3 ± 7.8 | 56.2 ± 10.7 | .18 |
| LV end-systolic dimension, mm | 48.9 ± 10.6 | 52.0 ± 8.3 | 46.0 ± 11.8 | .07 |
| Change in LV ejection fraction, % | 9.9 ± 9.9 | 1.9 ± 5.6 | 17.0 ± 6.9 | <.0001 |

Abbreviations:
HF = heart failure;
NYHA = New York Heart Association;
LBBB = left bundle branch block;
RBBB = right bundle branch block;
ACE = angiotensin converting enzyme;
ARB = angiotensin II receptor blockade;
LV = left ventricular.

Example 12

Predictors of CRT Responsiveness

Figure 18:
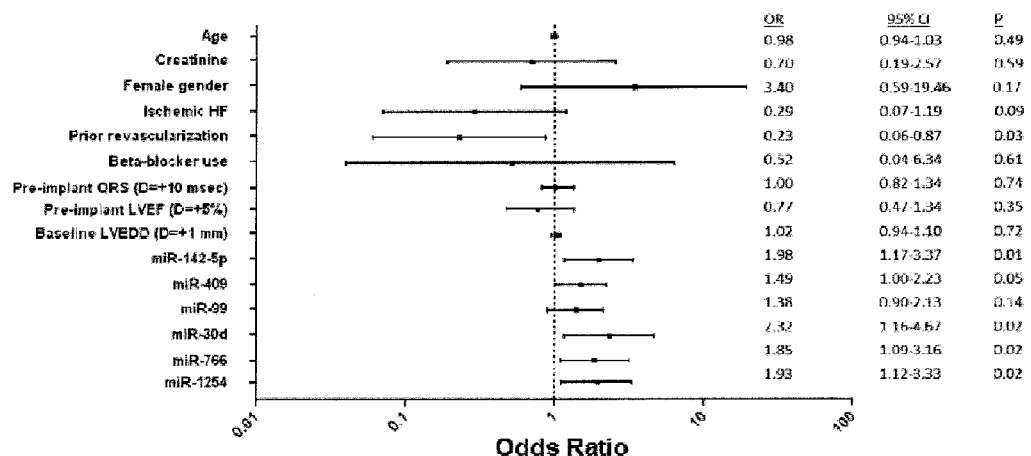
FIG. 18A is a graph showing a multivariate Cox regression analysis of parameters that would predict favorable LV remodeling in response to CRT.
FIG. 18B is a graph showing change in LV ejection fraction post-CRT as a function of miR-30d concentration.
Figure 18:
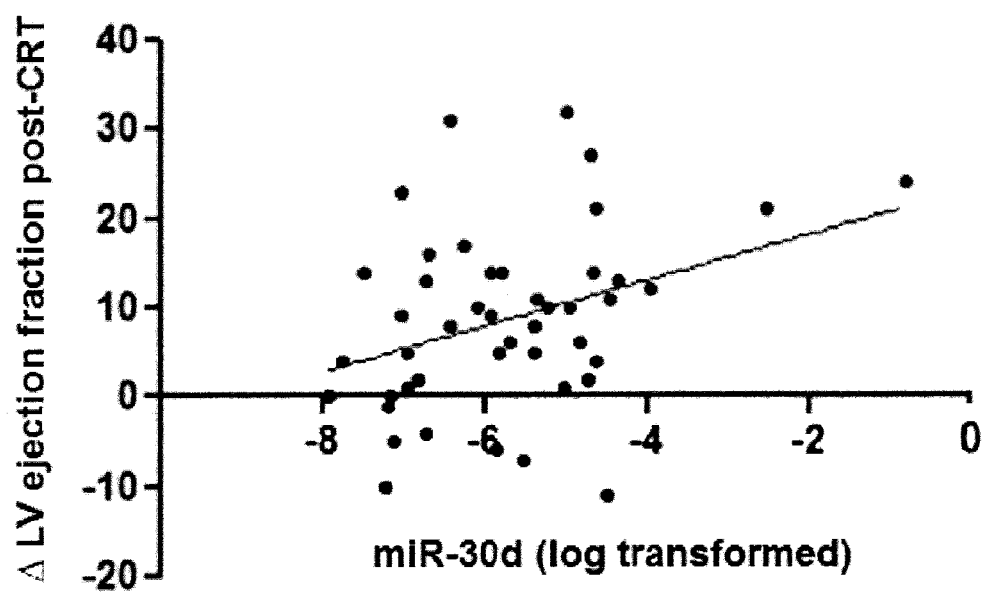

Multivariate Cox regression analyses was used to determine variables that could predict favorable LV remodeling in response to CRT, defined as an increase in LVEF≥10%. The presence of prior revascularization (P=0.03) was associated with a lower probability of CRT response; there was no association between other parameters of disease severity (including age, gender, etiology of HF, diabetes, atrial fibrillation, medication use, baseline pre-implant LVEF or QRS duration) and CRT responsiveness as defined above (Table 3), and FIG. 18A-forest plot). The concentrations of miR-30d (p=0.02), miR-766 (p=0.03) and miR-1254 (p=0.04) were associated with CRT responsiveness. In a best-overall multivariable logistic regression model including significant covariates in Table 3, only miR-30d emerged in the final model for association with CRT responsiveness. Finally, regression analysis using miR-30d concentrations as a continuous variable demonstrated a positive correlation between baseline levels of miR-30d and favorable LV remodeling at 6 months (FIG. 18B), a correlation that persisted even when removing either outlier. The predictive ability of miR-30d compared favorably with currently utilized clinical variables (EF and QRS duration) to predict an increase in EF of >10%. The C-statistic for miR-30d (0.7273) is non-significantly greater (p=0.1) than that of the model utilizing the clinical variables (C=0.5595), indicating that we have identified a circulating biomarker whose ability to predict CRT response at least equals that of currently used clinical variables.

TABLE 3

Univariable logistic regression for prediction of CRT response (defined as increase in LV ejection fraction ≥10%). Odds ratio represent odds of response to CRT.

| | CRT response | | |
|---|---|---|---|
| Covariate | OR | 95% CI | P value |
| Age | 0.98 | 0.94-1.03 | 0.49 |
| Female gender | 3.40 | 0.59-19.46 | 0.17 |
| Ischemic HF | 0.29 | 0.07-1.19 | 0.09 |
| Creatinine | 0.70 | 0.19-2.57 | 0.59 |
| Prior revascularization | 0.23 | 0.06-0.87 | 0.03 |
| Pre-implant QRS | 1.00 | 0.98-1.03 | 0.74 |
| AF | 1.08 | 0.29-4.08 | 0.91 |
| Diabetes mellitus | 1.08 | 0.29-4.08 | 0.91 |
| Beta-blocker use | 0.52 | 0.04-6.34 | 0.61 |
| Digoxin use | 0.23 | 0.04-1.31 | 0.10 |
| Diuretic use | 0.60 | 0.12-2.94 | 0.53 |
| Hypertension | 0.51 | 0.14-1.85 | 0.30 |
| ACE-I use | 0.42 | 0.12-1.53 | 0.19 |
| ARB use | 2.31 | 0.56-9.47 | 0.25 |
| Aldosterone antagonist use | 2.10 | 0.55-8.00 | 0.28 |
| Baseline LVEF | 0.95 | 0.86-1.06 | 0.35 |
| Baseline LVEDD | 1.02 | 0.94-1.10 | 0.72 |
| Baseline LVESD | 1.03 | 0.95-1.12 | 0.43 |
| miR-30d | 2.32 | 1.16-4.67 | 0.02 |
| miR-99 | 1.38 | 0.90-2.13 | 0.14 |
| miR-409 | 1.49 | 1.00-2.23 | 0.05 |

TABLE 3-continued

Univariable logistic regression for prediction of CRT response
(defined as increase in LV ejection fraction ≥10%).
Odds ratio represent odds of response to CRT.

| Covariate | CRT response | | |
|---|---|---|---|
| | OR | 95% CI | P value |
| miR-766 | 1.85 | 1.09-3.16 | 0.02 |
| miR-1254 | 1.93 | 1.11-3.33 | 0.02 |

Abbreviations:
OR = odds ratio;
CI = confidence interval;
HF = heart failure;
AF = atrial fibrillation;
ACE-I = angiotensin converting enzyme;
ARB = angiotensin II receptor blocker;
LVEF = LV ejection fraction;
LVEDD = LV end-diastolic dimension;
LVESD = LV end-systolic dimension.
NS = non-significant.

Example 13 miR-30d is Synthesized in the Heart and Secreted by Cardiomyocytes

Figure 19:
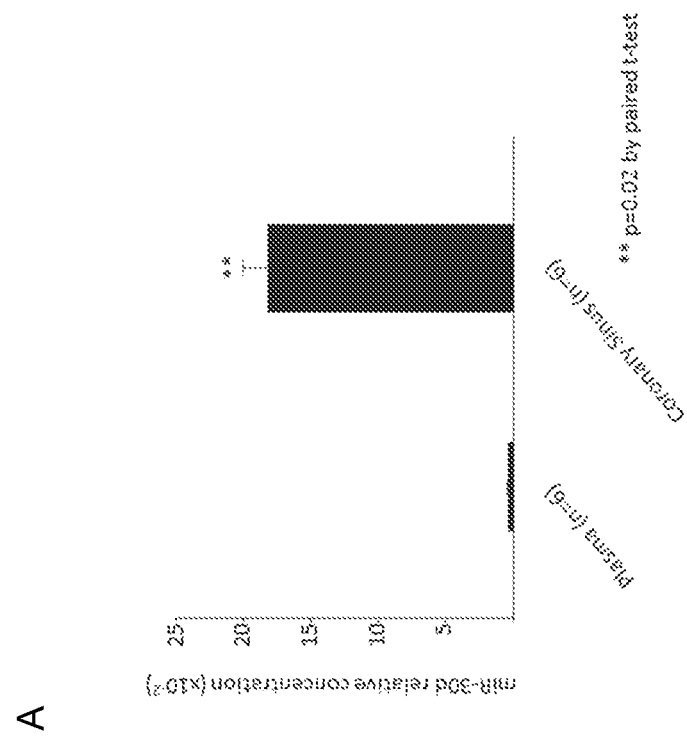
FIG. 19A is a graph showing the concentration of miR-30d in plasma and coronary sinus.
FIG. 19B is a graph showing the concentration of miR-30d in fibroblast and cardiomyocytes (CMs).

The source of circulating miR-30d was determined by examining the levels of the miRNA in coronary sinus plasma samples which were drawn at the time of CRT device placement, and are contemporaneous with our peripheral plasma samples. FIG. 19A demonstrates that levels of miR-30d are significantly higher in the coronary sinus than in circulating plasma (paired comparison of n=6 patients, p=0.02 by paired t-test) suggesting a cardiac origin for miR-30d.

Apart from cardiomyocytes (CMs), fibroblasts comprise the majority of non-CM cells in the heart. To determine the cellular origin of miR-30d, the expression of miR-30d was compared in a primary cultured CMs to primary cardiac fibroblasts derived from neonatal rat ventricles. miR-30d was expressed at significantly higher levels in CMs compared to fibroblasts fractions (FIG. 19B, n=4 independent experiments, p=0.02 for the paired comparison). The calculated ratio of 155-fold increased expression of miR-30d in CMs may in fact signify that the majority of miR-30d is synthesized and secreted by CMs rather than cardiac fibroblasts.

Example 14 miR-30d is Upregulated During CM Stretch

Figure 20:
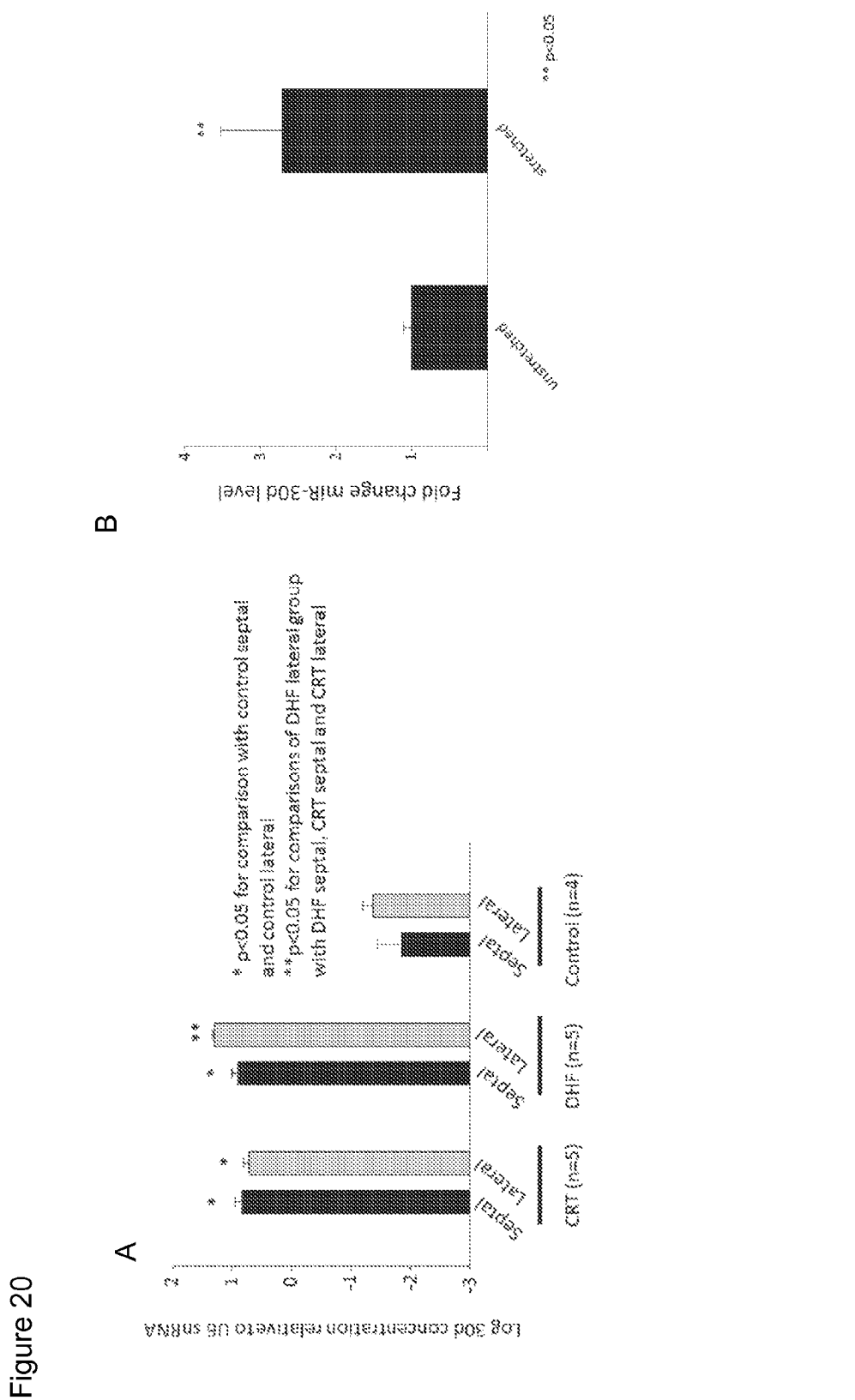
FIG. 20A is a graph showing the level of miR-30d in the septal and lateral walls of DHF and CRT dogs.
FIG. 20B is a graph showing the levels of miR-30d in unstretched and stretched silicone membranes.

In order to study the expression of miR-30d in an in vivo model of dyssynchrony, a model of canine dyssynchronous heart failure was used. In this model, DHF is induced by catheter ablation of the left bundle branch. Following ablation, three weeks of rapid atrial pacing will lead to heart failure, evidenced by a decline in ejection fraction and ventricular dilation. If ventricular synchrony is restored at the end of the three-week period and atrial pacing is resumed, partial recovery of ventricular function is observed (CRT group). RNA fractions were extracted from the septal and lateral walls of DHF and CRT dogs and compared the miR-30d levels (normalized to U6 snRNA). Results are shown in FIG. 20A. Compared to control dogs, the levels of miR-30d are markedly elevated in both DHF and CRT dogs (n=5 dogs in the DHF and CRT groups, and n=4 in the control group). In addition, the levels of miR-30d are highest in the lateral walls of DHF dogs (p<0.05 relative to the septal wall miR-30d levels in DHF dogs) and the difference between the lateral and septal walls is eliminated in CRT dogs. In the dyssynchronous dog model, left bundle branch ablation leads to the delayed contraction of the lateral wall, mimicking human left bundle branch QRS dyssynchrony. The upregulation if miR-30d is restored by CRT. miR-30d target MAP4K4 protein levels were decreased in a corresponding manner, although mRNA levels were not, suggesting that miR-30d acts by inhibiting translation of MAP4K4 mRNA.

The effect of wall stress was mimicked in an in vitro model by subjecting CMs seeded on a silicone membrane to cyclic stretch at 3 Hz. This technique has been previously described and leads to known changes in gene expression consistent with hypertrophy. After six hours of stretch, the supernatant fraction was collected and EMVs were isolated as previously described. An increase in miR-30d levels in the EMV fraction was found, consistent with the increased levels found in the canine model of DHF. miR-30d levels appear to be dynamically regulated. The dyssynchronous lateral wall is subjected to increased wall stress as a result of its delayed contraction, and this appears to be a stimulus for miR-30d secretion. The results demonstrate both increased tissue levels of miR-30d, as well as increased levels in the EMV fraction, suggesting that miR-30d may have paracrine as well as autocrine effects on the myocytes themselves, and potentially other cell types in the heart.

Example 15 miR-30d Causes Hypertrophy in Neonatal Rat Myocytes

Figure 21:
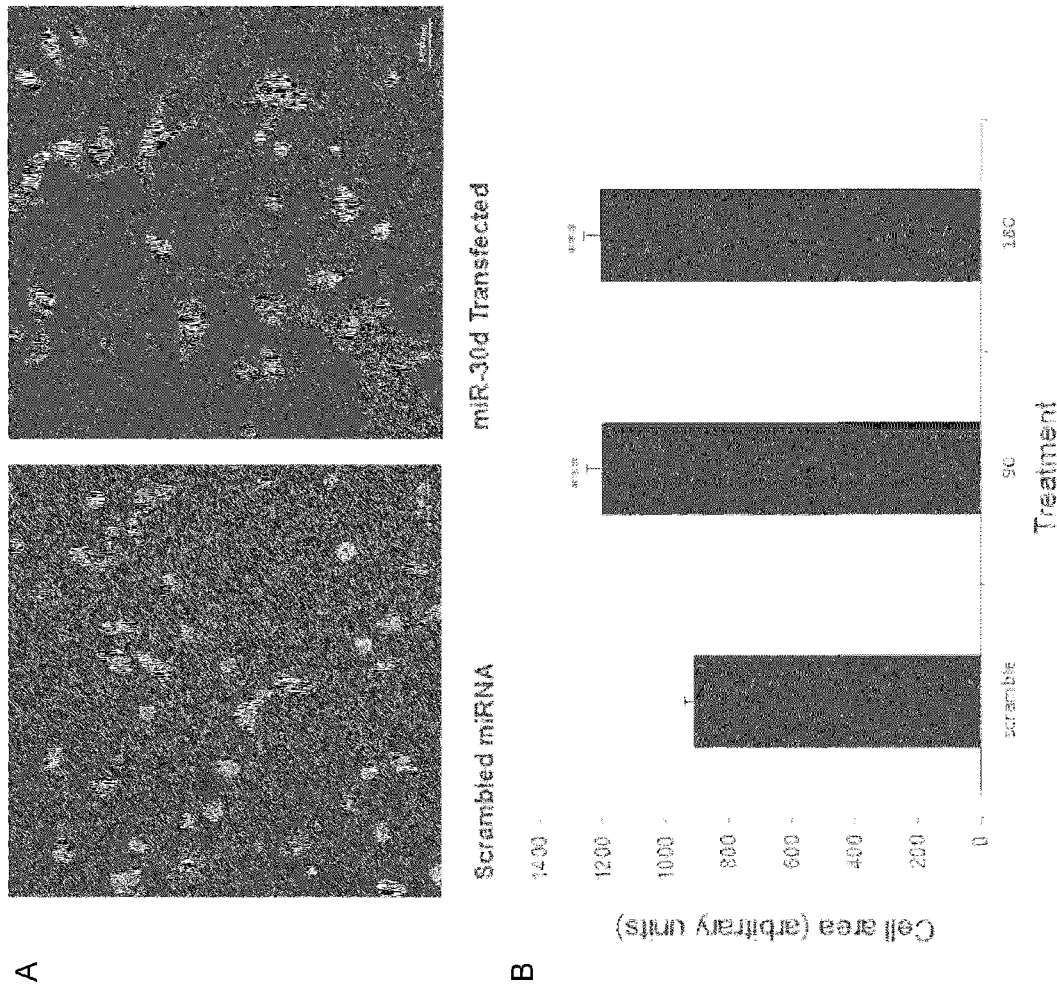
FIG. 21A are immunohistochemical staining of cells transfected with miR-30d.
FIG. 21B is a graph showing an increase in cell area as a function of miR-30d transfection after 90 minutes and 180 minutes indicating that miR-30d induces cardiomyocyte hypertrophy.

Because miR-30d appears to predict favorable LV remodeling, the effect of increased miR-30d in CMs were determined next. In order to study the effects of miR-30d on CM biology, a miR-30d precursor (miRNA mimic, Invitrogen, Inc) was transiently transfected into rat neonatal cardiomyocytes, using a liposomal delivery system (Lipofectamine 2000). CMs were harvested 48 hrs after transfection and RNA was extracted using the mirVANA Paris system. Using real-time PCR, robust expression of miR-30d in a dose-dependent manner compared to transfection of a mimic miRNA was demonstrated.
Immunohistochemical Staining for α-Actinin Demonstrated that miR-30d Induced Cardiomyocyte Hypertrophy (FIGS. 21A and 21B).

Figure 22:
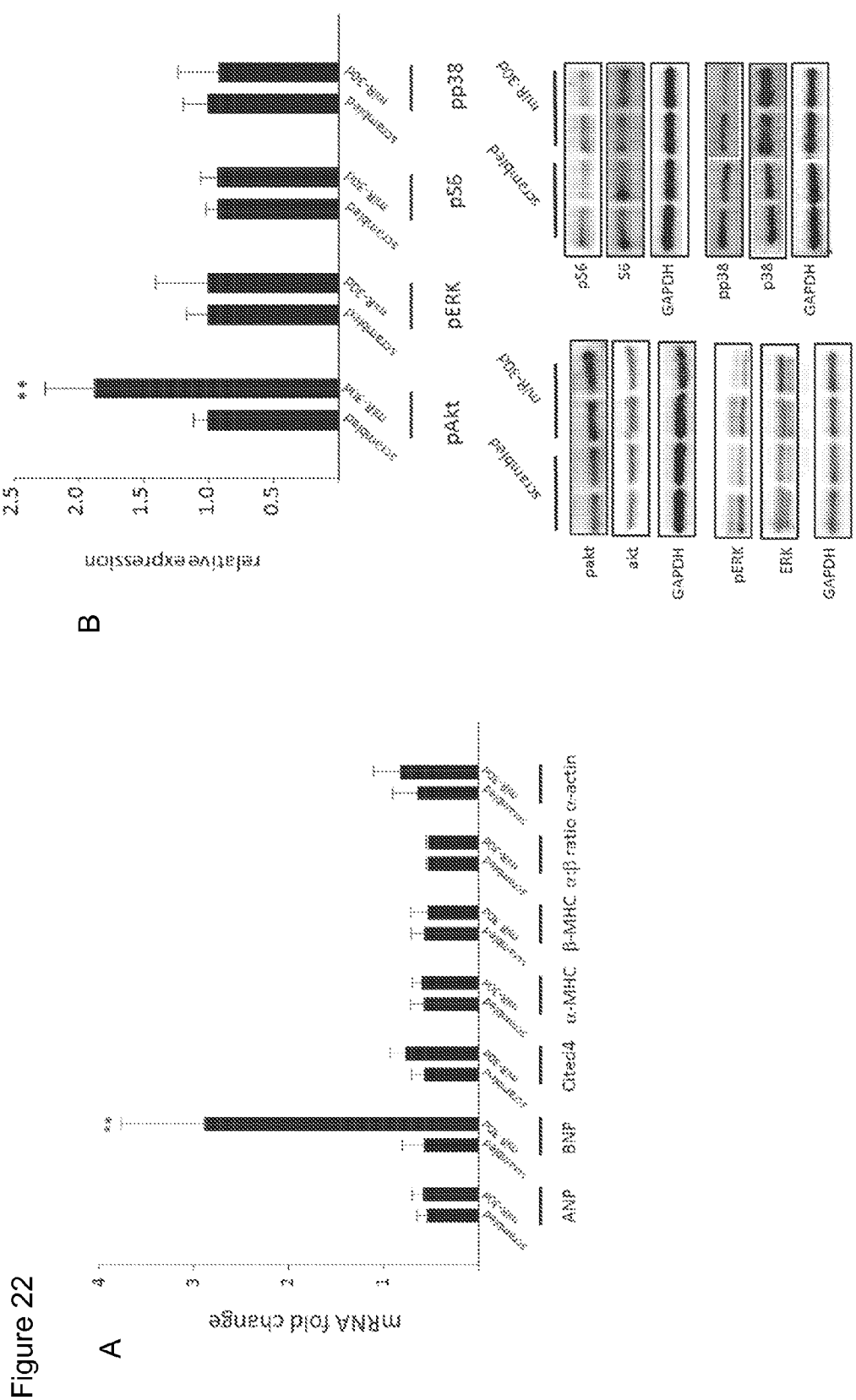
FIG. 22A is a graph showing levels of mRNA for a number of hypertrophy associated genes in response to miR30d administration.
FIG. 22B is a graph and Western blots showing expression of various genes associated with MAPK signaling in response to miR30d administration.

Myocyte hypertrophy has been correlated with characteristic changes in gene expression. The induction of pathologic hypertrophy is associated with an increase in fetal MHC isoforms and an increase in the expression of atrial natriuretic peptide (ANP) and brain natriuretic peptide (BNP). More recently, putative markers of physiological, rather than pathological, hypertrophy have been suggested. These include the transcriptional co-activator cited4, and α-actin. To examine the effect of miR-30d on CM gene expression, cells were harvested 48 hours post transfection, and the levels of miRNAs for a number of hypertrophy-associated genes were examined. It was found that while cell size had clearly increased, there was no significant change in the mRNA levels of either MHC isoform, or the α/β-MHC ratio (FIG. 22A). There was an increase in BNP, but not ANP, mRNA levels and no change in cited4 or α-actin mRNA, suggesting a hypertrophic phenotype that is not classically pathological or physiological.

miRNAs have been shown to modulate the activity of multiple intracellular signaling pathways. The MAPK signal transduction cascade is critical to the process of cardiac hypertrophy, and miRNAs such as miR-208a have been shown to modulate MAPK signaling by modulating upstream regulators. To investigate the effects of miR-30d on MAPK signaling, neonatal myocytes were transfected with either a synthetic miR-30d, or with a mimic oligonucleotide. Cells were lysed 48 hours after exposure and the levels of phosphorylated Akt, ERK, p70s6K, and p38 were examined. These levels were normalized to levels of GAPDH in the cell lysate. As shown in FIG. 22B, exposure to miR-30d leads to an increase in phosphorylated Akt, but not the other downstream signaling effectors in the MAPK cascade. These results demonstrate while miR-30d clearly mediates hypertrophy, this hypertrophy is intermediate between previously described pathological and physiological phenotypes.

Example 16

Downstream Targets of miR-30d

Figure 23:
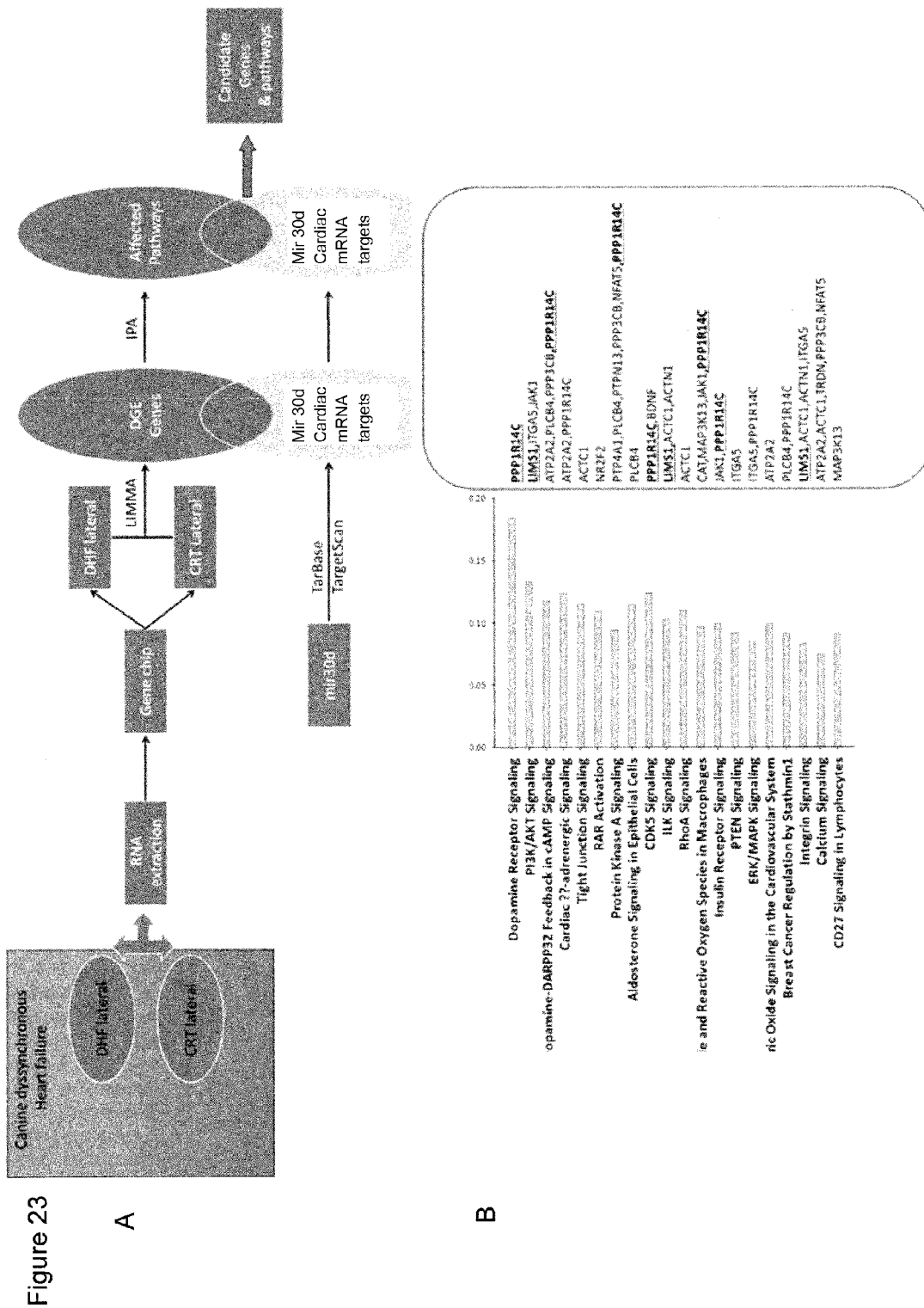
FIG. 23A is a schematic showing functional pathways that may be associated with miR-30d expression.
FIG. 23B is a chart showing pathways predicted to be affected by changes in miR-30d.

To further investigate the functional role of miR-30d, downstream molecules that are suppressed by miR-30d were identified. To this end, published microarray data in the dyssynchronous dog model was used. Using a LIMMA (linear models for microarray data) approach, genes whose expression was down-regulated in a manner coordinate with miR-30d levels (i.e., genes which were down-regulated in the lateral wall of dyssynchronous dogs where miR-30d levels were highest in relation to the septal wall) were searched. Within this subset of genes, putative miR-30d targets were screened as predicted by the Tarbase and TargetScan algorithms. Using the IPA (ingenuity pathways analysis) approach a set of predicted functional pathways that are associated with the observed changes in miR-30d expression (see cartoon in FIG. 23A) was generated. The graph in FIG. 23B displays the pathways most predicted to be affected by the changes in miR-30d. The bubble above the graph shows the specific gene products within the pathways that are affected. Several of these genes affect multiple biologically relevant pathways, specifically, LIMS1, PODXL, PPP1R14c, MAP3K13, JAK1, PGC1, and CAM-KIV. Furthermore, miR-30d has recently been shown to suppress expression of MAP4K4 in pancreatic tissue and MAP4K4 mRNA has a predicted high affinity binding site for miR-30d. For this reason, MAP4K4 was also included in the list of potential targets.

Figure 24:
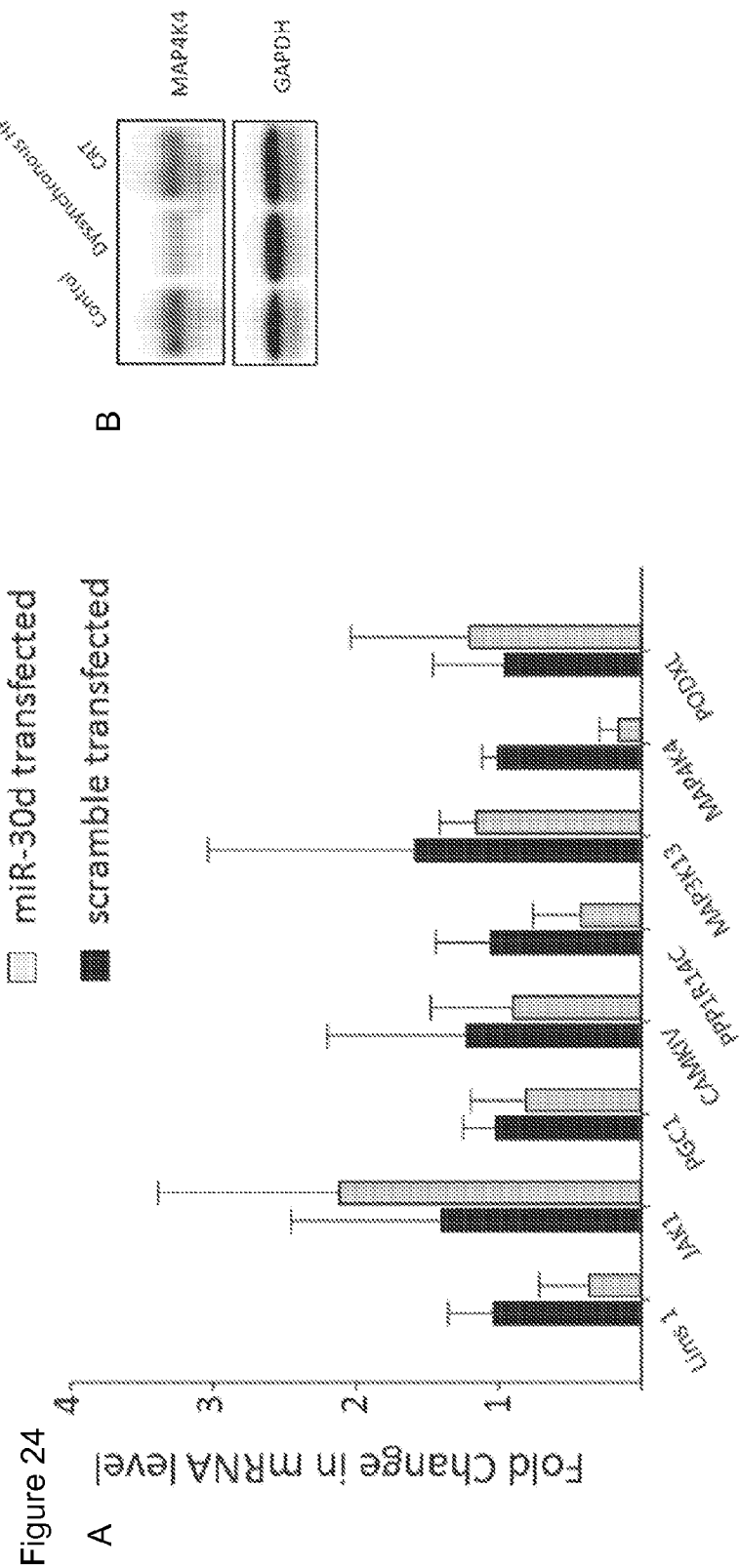
FIG. 24A is a graph showing mRNA levels of genes particularly affected by miR-30d upon transient transfection of CMs with miR-30d.
FIG. 24B is a Western blot showing MAP4K4 protein expression in the dyssynchronous dog heart and CRT dogs.

To determine if miR-30d could effectively silence the miRNAs for the putative targets identified above, the cell culture system was used. Transient transfection of CMs with miR-30d caused a significant decrease in the mRNA levels of LIMS1, MAP4K4, and PPP1R14c (FIG. 24A) relative to scramble transfected cells. Interestingly, while MAP4K4 mRNA levels were not down-regulated in the lateral wall of the dyssynchronous dog heart, protein levels were significantly decreased (FIG. 24B). The modulation of protein expression by miRNAs may occur by either increased mRNA degradation or inhibition of ribosomal translation; it would appear that the latter mechanism is involved in miR-30d modulation of MAP4K4 in the canine heart. The decrease in MAP4K4 protein expression was attenuated in CRT dogs, where miR-30d levels are lower compared to DHF. In a transient transfection model, miR-30d mediates myocyte hypertrophy. The gene expression pattern appears to have characteristics of both pathologic as well as physiologic hypertrophy.

Figure 25:
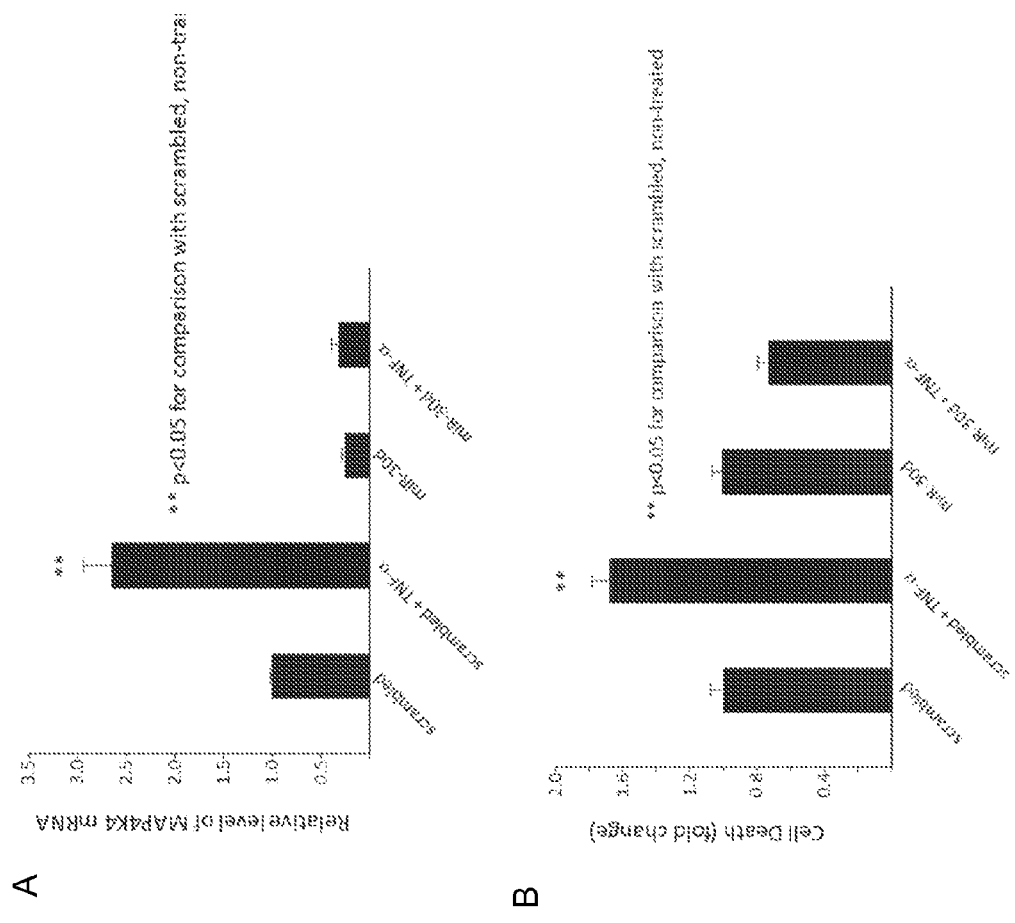
FIG. 25A is a graph showing the level of MAP4K4 mRNA upon transient transfection with TNF-α and/or miR-30d.
FIG. 25B is a graph showing apoptosis level upon transient transfection with TNF-α and/or miR-30d.

MAP4K4 has previously been shown to have a role in the transduction of TNF-α signaling. TNF-α increases MAP4K4 levels, which leads to a downstream increase in IRS-2 and MafA in pancreatic β-cells and can induce apoptosis in several cell types. TNF-α levels are known to be upregulated in the lateral wall of dyssynchronous dog hearts and in the lateral wall of human hearts with left bundle branch block and dyssynchrony. It was hypothesized that miR-30d plays a protective role in the dyssynchronous lateral wall, preventing TNF-α-induced apoptosis while simultaneously promoting adaptive myocyte hypertrophy. Treatment of scramble transfected CMs with TNF-α lead to a robust increase in MAP4K4 mRNA, which was attenuated by overexpression of miR-30d (FIG. 25A). Resulting MAP4K4 levels were reduced beyond baseline expression levels in the cell to a level similar to that seen in the initial miR-30d target screen. To assess apoptosis levels in CMs, commercially available ELISA based apoptosis assay was used that detects the characteristic nucleosome-DNA fragments liberated as part of the apoptotic process. Results of this assay are shown in FIG. 25B. As expected, there is an increase in apoptosis with TNF-α treatment; however, this increase is abrogated by miR-30d transfection.

miR-30d, by downregulating MAP4K4, is able to partially reverse TNF-α induced apoptosis. The role of TNF-α in myocyte apoptosis has been well described. Levels of TNF-α are known to be increased in hearts subjected to pathologic hypertrophic stimuli in multiple models, as well as in the lateral wall in the canine dyssynchrony model. Thus, a human miRNA, miR-30d has been identified, whose levels predict the response to CRT in a manner independent of current clinical predictors, and with an equal predictive accuracy. miR-30d is selectively upregulated in the late contracting lateral wall in the canine dyssynchrony model, and appears to mediate myocyte hypertrophy while simultaneously blocking the deleterious effects of TNF-α on the myocyte. The findings lend themselves to the attractive hypothesis that miR-30d allows for an adaptive hypertrophy where it is needed (in late-contracting areas of the heart), while simultaneously preventing TNF-α induced apoptosis. Patients with left ventricular dyssynchrony and higher miR-30d levels may represent a subpopulation of patients with DHF who may have more reversible changes and will thus respond better to CRT than those with lower levels.

OTHER EMBODIMENTS

All publications and patents cited in this specification are incorporated herein by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for predicting a response to a cardiac therapy in a patient suffering from a cardiac disease, comprising:
   i) reverse transcribing one or more biomarkers having at least 85% sequence identity to one or more sequences of SEQ ID NOs: 1, 27, and/or 33 to one or more DNA products by contacting a sample from the patient comprising the one or more biomarkers having at least 85% sequence identity to one or more sequences of SEQ ID NOs: 1, 27, and/or 33 with at least one primer having a sequence that is complementary to one or more sequences of SEQ ID NOs: 1, 27, and/or 33;
   ii) amplifying the one or more DNA products from i) by quantitative polymerase chain reaction (qPCR) to detect the level of expression of the one or more biomarkers in the patient sample; and
   iii) comparing the level of expression of the one or more biomarkers in the patient sample to a control sample to predict the response to the cardiac therapy in the patient,
   wherein an increase in the level of expression of the one or more biomarkers in the patient sample relative to the control sample is a prediction of a positive response to the cardiac therapy in the patient.

2. The method of claim 1, wherein the method further comprises administering the cardiac therapy to the patient based on the prediction of the positive response to the cardiac therapy.

3. The method of claim 1, wherein the predicting is done prior to a first cardiac therapy, after the first cardiac therapy, and/or during the course of any cardiac therapy.

4. The method of claim 1, wherein the cardiac therapy comprises cardiac resynchronization therapy (CRT) or miRNA based therapy.

5. The method of claim 1, wherein the biomarker has the sequence of SEQ ID NO: 1.

6. The method of claim 1, wherein the cardiac disease is heart failure or dyssynchronous heart failure.

7. The method of claim 1, wherein the patient sample is a blood sample or a plasma sample.

8. The method of claim 1, wherein the biomarker has at least 85% sequence identity to
   a) the sequences of SEQ ID NOs:1 and 27; or
   b) the sequences of SEQ ID NOs: 1 and 33; or
   c) the sequences of SEQ ID NOs: 27 and 33.

* * * * *

SEQUENCE LISTING

```
<160> NUMBER OF SEQ ID NOS: 34

<210> SEQ ID NO 1
<211> LENGTH: 22
<212> TYPE: RNA
<213> ORGANISM: Homo sapiens

<400> SEQUENCE: 1
uguaaacauc cccgacugga ag                                              22

<210> SEQ ID NO 2
<211> LENGTH: 70
<212> TYPE: RNA
<213> ORGANISM: Homo sapiens

<400> SEQUENCE: 2
guuguuguaa acaucccega cuggaagcug uaagacacag cuaagcuuuc agucagaugu      60
uugcugcuac                                                            70

<210> SEQ ID NO 3
<211> LENGTH: 23
<212> TYPE: DNA
<213> ORGANISM: Homo sapiens

<400> SEQUENCE: 3
aactccctca agattgtcag caa                                             23

<210> SEQ ID NO 4
<211> LENGTH: 20
<212> TYPE: DNA
<213> ORGANISM: Homo sapiens

<400> SEQUENCE: 4
ggctaagcag ttggtggtgc                                                 20

<210> SEQ ID NO 5
<211> LENGTH: 22
<212> TYPE: DNA
<213> ORGANISM: Homo sapiens

<400> SEQUENCE: 5
aagaacctgc tagaccacct gg                                              22

<210> SEQ ID NO 6
<211> LENGTH: 22
<212> TYPE: DNA
<213> ORGANISM: Homo sapiens

<400> SEQUENCE: 6
gcttcctcag tctgctcact ca                                              22

<210> SEQ ID NO 7
<211> LENGTH: 20
<212> TYPE: DNA
<213> ORGANISM: Homo sapiens

<400> SEQUENCE: 7
ccgagtccca ggtcaacaag                                                 20

<210> SEQ ID NO 8
<211> LENGTH: 22
<212> TYPE: DNA
<213> ORGANISM: Homo sapiens
```

```
<400> SEQUENCE: 8
tcatcgtgca ttttctgctt gg                                      22

<210> SEQ ID NO 9
<211> LENGTH: 20
<212> TYPE: DNA
<213> ORGANISM: Homo sapiens

<400> SEQUENCE: 9
gagagatggc tgcatttggg                                         20

<210> SEQ ID NO 10
<211> LENGTH: 20
<212> TYPE: DNA
<213> ORGANISM: Homo sapiens

<400> SEQUENCE: 10
gtcaccgtct tgccattctc                                         20

<210> SEQ ID NO 11
<211> LENGTH: 20
<212> TYPE: DNA
<213> ORGANISM: Homo sapiens

<400> SEQUENCE: 11
gccttatggg gagtgaattt                                         20

<210> SEQ ID NO 12
<211> LENGTH: 20
<212> TYPE: DNA
<213> ORGANISM: Homo sapiens

<400> SEQUENCE: 12
acccctgctt cttctcaact                                         20

<210> SEQ ID NO 13
<211> LENGTH: 20
<212> TYPE: DNA
<213> ORGANISM: Homo sapiens

<400> SEQUENCE: 13
caactgcggg aaggagctaa                                         20

<210> SEQ ID NO 14
<211> LENGTH: 20
<212> TYPE: DNA
<213> ORGANISM: Homo sapiens

<400> SEQUENCE: 14
ggcattcact actcgccctt                                         20

<210> SEQ ID NO 15
<211> LENGTH: 20
<212> TYPE: DNA
<213> ORGANISM: Homo sapiens

<400> SEQUENCE: 15
aggcaagagt gcatagagcg                                         20

<210> SEQ ID NO 16
<211> LENGTH: 20
<212> TYPE: DNA
```

```
<213> ORGANISM: Homo sapiens

<400> SEQUENCE: 16
gggtcttgtc cttgagtggg                                          20

<210> SEQ ID NO 17
<211> LENGTH: 20
<212> TYPE: DNA
<213> ORGANISM: Homo sapiens

<400> SEQUENCE: 17
gtaggcccag gtatgacagc                                          20

<210> SEQ ID NO 18
<211> LENGTH: 20
<212> TYPE: DNA
<213> ORGANISM: Homo sapiens

<400> SEQUENCE: 18
ctctctgcgg tattcgtccc                                          20

<210> SEQ ID NO 19
<211> LENGTH: 20
<212> TYPE: DNA
<213> ORGANISM: Homo sapiens

<400> SEQUENCE: 19
gacttcaatc aaaggcggcg                                          20

<210> SEQ ID NO 20
<211> LENGTH: 20
<212> TYPE: DNA
<213> ORGANISM: Homo sapiens

<400> SEQUENCE: 20
gaggatcccg tttagagccg                                          20

<210> SEQ ID NO 21
<211> LENGTH: 20
<212> TYPE: DNA
<213> ORGANISM: Homo sapiens

<400> SEQUENCE: 21
gctcctcaag ggaggattcg                                          20

<210> SEQ ID NO 22
<211> LENGTH: 20
<212> TYPE: DNA
<213> ORGANISM: Homo sapiens

<400> SEQUENCE: 22
tttcttcttc ctcgcagcca                                          20

<210> SEQ ID NO 23
<211> LENGTH: 20
<212> TYPE: DNA
<213> ORGANISM: Homo sapiens

<400> SEQUENCE: 23
acagacgtgg cagagtaagc                                          20

<210> SEQ ID NO 24
<211> LENGTH: 20
```

```
<212> TYPE: DNA
<213> ORGANISM: Homo sapiens

<400> SEQUENCE: 24
ctgcagaggc aatgtccaga                                                    20

<210> SEQ ID NO 25
<211> LENGTH: 20
<212> TYPE: DNA
<213> ORGANISM: Homo sapiens

<400> SEQUENCE: 25
atcctgccat aaagccccac                                                    20

<210> SEQ ID NO 26
<211> LENGTH: 20
<212> TYPE: DNA
<213> ORGANISM: Homo sapiens

<400> SEQUENCE: 26
agggctcccc ttacaaaagc                                                    20

<210> SEQ ID NO 27
<211> LENGTH: 24
<212> TYPE: RNA
<213> ORGANISM: Homo sapiens

<400> SEQUENCE: 27
agccuggaag cuggagccug cagu                                               24

<210> SEQ ID NO 28
<211> LENGTH: 21
<212> TYPE: RNA
<213> ORGANISM: Homo sapiens

<400> SEQUENCE: 28
cauaaaguag aaagcacuac u                                                  21

<210> SEQ ID NO 29
<211> LENGTH: 22
<212> TYPE: RNA
<213> ORGANISM: Homo sapiens

<400> SEQUENCE: 29
ugaccgauuu cuccuggugu uc                                                 22

<210> SEQ ID NO 30
<211> LENGTH: 97
<212> TYPE: RNA
<213> ORGANISM: Homo sapiens

<400> SEQUENCE: 30 gguggagga uugcuugagc cuggaagcug gagccugcag ugaacuauca uugugccacu         60
guacuccagc cuaggcaaca aaaugaaauc cugucua                                 97

<210> SEQ ID NO 31
<211> LENGTH: 87
<212> TYPE: RNA
<213> ORGANISM: Homo sapiens

<400> SEQUENCE: 31
gacagugcag ucacccauaa aguagaaagc acuacuaaca gcacuggagg guguaguguu        60
```

```
uccuacuuua uggaugagug uacugug                                               87

<210> SEQ ID NO 32
<211> LENGTH: 88
<212> TYPE: RNA
<213> ORGANISM: Homo sapiens

<400> SEQUENCE: 32
aucucuuaca caggcugacc gauuucuccu gguguucaga gucuguuuuu gucuagcacc           60
auuugaaauc gguuaugaug uaggggga                                             88

<210> SEQ ID NO 33
<211> LENGTH: 22
<212> TYPE: RNA
<213> ORGANISM: Homo sapiens

<400> SEQUENCE: 33
acuccagccc cacagccuca gc                                                   22

<210> SEQ ID NO 34
<211> LENGTH: 111
<212> TYPE: RNA
<213> ORGANISM: Homo sapiens

<400> SEQUENCE: 34
gcauccucag gaccugggcu ugggugguag gaggaauugg ugcuggucuu ucauuuugga           60
uuugacucca gccccacagc cucagccacc ccagccaauu gucauaggag c                   111
```